(12) United States Patent
Hanbury

(10) Patent No.: US 10,799,667 B2
(45) Date of Patent: *Oct. 13, 2020

(54) METHODS AND SYSTEMS FOR MODULATING STIMULI TO THE BRAIN WITH BIOSENSORS

(71) Applicant: Sana Health, Inc., San Rafael, CA (US)

(72) Inventor: Richard Hanbury, San Rafael, CA (US)

(73) Assignee: SANA HEALTH, INC., Lafayette, CO (US)

( * ) Notice: Subject to any disclaimer, the term of this patent is extended or adjusted under 35 U.S.C. 154(b) by 374 days.

This patent is subject to a terminal disclaimer.

(21) Appl. No.: 15/910,252

(22) Filed: Mar. 2, 2018

(65) Prior Publication Data

US 2018/0250494 A1 Sep. 6, 2018

Related U.S. Application Data

(60) Provisional application No. 62/466,281, filed on Mar. 2, 2017.

(51) Int. Cl.
*A61M 21/02* (2006.01)
*A61M 21/00* (2006.01)
(Continued)

(52) U.S. Cl.
CPC .......... *A61M 21/02* (2013.01); *A61B 5/0245* (2013.01); *A61B 5/02405* (2013.01); *A61B 5/04845* (2013.01); *A61B 5/16* (2013.01); *A61B 5/4836* (2013.01); *A61B 5/6803* (2013.01); *A61B 5/01* (2013.01); *A61B 5/02438* (2013.01); *A61B 5/0482* (2013.01); *A61B 5/0488* (2013.01); *A61M 2021/0022* (2013.01);
(Continued)

(58) Field of Classification Search
CPC ............................................... A61M 21/00–02
See application file for complete search history.

(56) References Cited

U.S. PATENT DOCUMENTS

| 4,172,406 A | 10/1979 | Martinez |
| 4,315,502 A | 2/1982 | Gorges |

(Continued)

FOREIGN PATENT DOCUMENTS

| WO | 2001064005 A2 | 9/2001 |
| WO | 2012117343 A1 | 9/2012 |
| WO | 2019060598 A1 | 3/2019 |

OTHER PUBLICATIONS

PCT Search Report & Written Opinion, PCT/US2018/020547.
(Continued)

*Primary Examiner* — Thaddeus B Cox
(74) *Attorney, Agent, or Firm* — Dickinson Wright PLLC

(57) ABSTRACT

Visual and auditory stimuli are provided to a patient to treat various neurological disorders or conditions and/or to provide improved mental or physical performance. The visual and auditory stimuli are provided by a wearable headset or sleep mask that may be comfortably worn by a user, such as in bed to induce sleep. The wearable headset or sleep mask includes, or works in cooperation with, sensors that determine the state of the user and modify the operation of the headset for treating various disorders or contentions.

23 Claims, 9 Drawing Sheets

(51) Int. Cl.
| | |
|---|---|
| *A61B 5/0245* | (2006.01) |
| *A61B 5/16* | (2006.01) |
| *A61B 5/0484* | (2006.01) |
| *A61B 5/024* | (2006.01) |
| *A61B 5/00* | (2006.01) |
| *A61B 5/0482* | (2006.01) |
| *A61B 5/0488* | (2006.01) |
| *A61B 5/01* | (2006.01) |

(52) U.S. Cl.
CPC ............... *A61M 2021/0027* (2013.01); *A61M 2021/0044* (2013.01); *A61M 2205/3368* (2013.01); *A61M 2205/3561* (2013.01); *A61M 2230/10* (2013.01)

(56) References Cited

U.S. PATENT DOCUMENTS

| | | | |
|---|---|---|---|
| 4,892,106 A | 1/1990 | Gleeson, III | |
| 5,343,261 A | 8/1994 | Wilson | |
| 5,783,909 A | 7/1998 | Hochstein | |
| 6,123,661 A * | 9/2000 | Fukushima | A61M 21/00 600/26 |
| 8,562,659 B2 | 10/2013 | Wells et al. | |
| 8,838,247 B2 | 9/2014 | Hagedorn et al. | |
| 10,328,236 B2 | 6/2019 | Hanbury | |
| 2002/0198577 A1* | 12/2002 | Jaillet | A61M 21/00 607/88 |
| 2006/0106276 A1 | 5/2006 | Shealy et al. | |
| 2008/0269629 A1* | 10/2008 | Reiner | A61B 5/4836 600/544 |
| 2010/0323335 A1 | 12/2010 | Lee | |
| 2011/0075853 A1 | 3/2011 | Anderson | |
| 2011/0213664 A1 | 9/2011 | Osterhout | |
| 2012/0095534 A1 | 4/2012 | Schlangen et al. | |
| 2012/0211013 A1 | 8/2012 | Otis | |
| 2013/0035734 A1 | 2/2013 | Soler Fernandez et al. | |
| 2013/0225915 A1* | 8/2013 | Redfield | A61N 5/0618 600/28 |
| 2013/0267759 A1 | 10/2013 | Jin | |
| 2014/0336473 A1 | 11/2014 | Greco | |
| 2015/0231395 A1 | 8/2015 | Saab | |
| 2015/0268673 A1 | 9/2015 | Farzbod et al. | |
| 2017/0143935 A1 | 5/2017 | Hanbury | |
| 2017/0252532 A1* | 9/2017 | Holsti | A61G 11/008 |
| 2017/0312476 A1* | 11/2017 | Woo | A61M 21/02 |
| 2019/0030279 A1 | 1/2019 | Nowlin | |

OTHER PUBLICATIONS

PCT Search Report & Written Opinion, PCT/US2016063651.
The International Searching Authority, Notification of Transmittal of the International Search Report and the Written Opinion of the International Searching Authority dated Aug. 2, 2019 in International Application No. PCT/US19/033322, 19 pages.
Chinnakkaruppan Adaikkan, et al., "Gamma Entrainment Binds Higher-Order Brain Regions and Offers Neuroprotection", Neuron, https://linkinghub.elsevier.com/retrieve/pii/S0896627319303460, May 7, 2019 (May 7, 2019), 18 Pages.
Liviu Aron, et al., "Neural synchronization in Alzheimer's disease", Nature, Journal, vol. 540, Dec. 7, 2016 (Dec. 7, 2016), pp. 207-208.
Pam Belluck, "Could simply listening to this sound help cure Alzheimer's disease? MIT researchers are investigating", Boston Globe, https://www.bostonglobe.com/news/science/2019/03/14/could-simply-listening-this-sound-help-cure-alzheimer-disease-mit-researchers-are-investigating/2npZrAp8g9kLSfURbTxaVO/story.html, Mar. 14, 2019 (Mar. 14, 2019), 4 Pages.
Pam Belluck, "A Possible Alzheimer's Treatment With Clicks and Flashes? It Worked on Mice", New York Times, https://www.nytimes.com/2019/03/14/health/alzheimers-memory.html, Mar. 14, 2019 (Mar. 14, 2019), 5 Pages.

Angus Chen, "An Hour of Light and Sound a Day Might Keep Alzheimer's at Bay", Scientific American, https://www.scientificamerican.com/article/an-hour-of-light-and-sound-a-day-might-keep-alzheimers-at-bay/, Mar. 14, 2019 (Mar. 14, 2019), 5 Pages.
Aimee Corso, "Cognito Therapeutics Launched with Exclusive License to Promising Alzheimer's Research from The Massachusetts Institute of Technology ", Business Wire, Boston and San Francisco, https://www.businesswire.com/news/home/20161207006042/en/Cognito-Therapeutics-Launched-Exclusive-License-Promising-Alzheimer%E2%80%99s, Dec. 7, 2016 (Dec. 7, 2016), 3 Pages.
Hannah Devlin, "Strobe lighting provides a flicker of hope in the fight against Alzheimer's", The Guardian, https://www.theguardian.com/science/2016/dec/07/strobe-lighting-provides-a-flicker-of-hope-in-the-fight-against-alzheimers, Dec. 7, 2016 (Dec. 7, 2016), 3 Pages.
Jamie Ducharme, "The End of Alzheimer's?", Boston, Magazine, https://www.bostonmagazine.com/health/2017/11/27/li-huei-tsai-alzheimers-treatment/, Nov. 27, 2017 (Nov. 7, 2017), 4 Pages.
Damian Garde, "'Beyond amyloid': A look at what's next in Alzheimer's research", STAT, https://www.statnews.com/2017/08/18/beyond-amyloid-alzheimers-research/, Aug. 18, 2017 (Aug. 18, 2017), 5 Pages.
Melissa Healy, "Flickering lights may illuminate a path to Alzheimer's treatment", Los Angeles Times, Dec. 7, 2016 (Dec. 7, 2016), 3 Pages.
Nathan Hurst, "Could Flickering Lights Help Treat Alzheimer's?", Smithsonian, https://www.smithsonianmag.com/innovation/could-flickering-lights-help-treat-alzheimers-180961762/, Jan. 11, 2017 (Jan. 11, 2017), 2 Pages.
Hannah F. Iaccarino, et al., "Gamma frequency entrainment attenuates amyloid load and modifies microglia", Nature, Journal, vol. 540, Dec. 7, 2016 (Dec. 7, 2016), pp. 230-235.
Anthony J. Martorell, et al., "Multi-sensory Gamma Stimulation Ameliorates Alzheimer's-Associated Pathology and Improves Cognition", Cell, https://www.cell.com/cell/fulltext/S0092-8674(19)30163-1, Mar. 14, 2019 (Mar. 14, 2019), 16 Pages.
Helen Thomson, "How flashing lights and pink noise might banish Alzheimer's, improve memory and more", Nature, https://www.nature.com/articles/d41586-018-02391-6, Feb. 28, 2018 (Feb. 28, 2018), 10 Pages.
Meg Tirrell, "Could flashing light treat Alzheimer's? Fresh approaches to treating the disease", CNBC, https://www.cnbc.com/2017/03/29/could-flashing-light-treat-alzheimers-fresh-approaches-to-treating-the-disease.html, Mar. 29, 2017 (Mar. 29, 2017), 6 Pages.
Anne Trafton, "Ed Boyden receives 2018 Canada Gairdner International Award", McGovern Institute, https://mcgovern.mit.edu/2018/03/27/ed-boyden-receives-2018-canada-gairdner-international-award/, Mar. 27, 2018 (Mar. 27, 2018), 3 Pages.
Molly Webster, et al., "Bringing Gamma Back", WNYC Studios, https://www.wnycstudios.org/story/bringing-gamma-back, Dec. 8, 2016 (Dec. 8, 2016), 3 Pages.
Robert Weisman, "MIT team uses LEDs to attack Alzheimer's ", Boston Globe, https://www.bostonglobe.com/business/2016/12/07/led-technology-from-mit-used-startup-working-alzheimer-treatment/Kbdjp9WvfoPLfC1bNhvGOI/story.html, Dec. 7, 2016 (Dec. 7, 2016), 4 Pages.
Nicole Wetsman, "Flickering light seems to help mice with Alzheimer's-like symptoms", Popular Science, https://www.popsci.com/flickering-light-genes-alzheimers, May 7, 2019 (May 7, 2019), 2 Pages.
Ed Yong, "Beating Alzheimer's With Brain Waves", The Atlantic, https://www.theatlantic.com/science/archive/2016/12/beating-alzheimers-with-brain-waves/509846/, Dec. 7, 2016 (Dec. 7, 2016), 8 Pages.
NSTC, "First Friday Biosciences: Nov. 3 in Woburn", https://www.nstc.org/previous-events/first-friday-biosciences-nov-3-in-woburn/, Nov. 3, 2017 (Nov. 3, 2017), 8 Pages.
The Picower Institute, "Tsai earns Hans Wigzell Research Foundation Science Prize", https://picower.mit.edu/news/tsai-earns-hans-wigzell-research-foundation-science-prize, Jan. 23, 2019 (Jan. 23, 2019), 3 Pages.

(56) References Cited

OTHER PUBLICATIONS

European Patent Office, Supplementary European Search Report dated Jun. 5, 2019 for European Patent Application No. 16869299.4, 8 pages.
International Searching Authority, Search Report and Written Opinion in PCT/US2020/019091, dated May 6, 2020; 13 pages.

* cited by examiner

METHODS AND SYSTEMS FOR MODULATING STIMULI TO THE BRAIN WITH BIOSENSORS

BACKGROUND OF THE INVENTION

Field of the Invention

The present disclosure relates to medical and consumer devices and methods. In particular, the present disclosure relates to modulating, with biosensor feedback, neurological stimuli to a subject to treat various neurological disorders or conditions and/or to provide relaxation and/or performance enhancement.

Discussion of the Background

Sensory stimulation has been used to treat various disorders. For example, binaural beats have applied to induce various mental states to encourage sleep, relaxation, meditation, creativity, and other desirable mental states. Combinations of auditory and visual stimuli have been applied to encourage such mental states as well. The application of such therapy, however, has been less than ideal in many circumstances. Equipment to provide the stimulus can be bulky, expensive, generally inaccessible, and below the critical efficacy threshold for widespread use, typically only helping subsets of the population. Users may find the use of such equipment difficult in many circumstances, such as when trying to sleep in a bedroom or an airplane cabin.

To treat various neurological disorders and conditions, pharmaceuticals and/or supplements are often used instead of sensory stimulation. The use of pharmaceuticals, however, can be less than ideal in many circumstances. Often, pharmaceuticals are expensive, rely on patient-compliance, and may require a prescription from a medical professional. Pharmaceuticals may be effective in only a small, less than ideal portion of the general population. To treat insomnia, for example, pharmaceuticals and supplements such as melatonin and Zolpidem (e.g., AMBIEN™) have questionable efficacy. Pharmaceuticals often lead to undesirable side effects. For example, some pharmaceutical for treating insomnia can lead to deprivation in certain ranges of deep sleep and increases in mortality rates.

For at least these reasons, improved methods and systems to treat neurological disorders and other conditions that overcome at least some of the aforementioned challenges are desired.

BRIEF SUMMARY OF THE INVENTION

The present disclosure relates to medical devices and methods which may be used, for example, to provide stimulus to a subject to treat various neurological disorders or conditions, where the stimulus provided may include one or more of an auditory, a visual, or a tactile stimulus. In certain embodiments, sensory stimulation is tailored to an individual's response to that stimulus, resulting in greatly enhanced benefits to the user. Certain embodiments include biosensors that measure heart rate, heart rate variability, temperature, brain activity (detected, for example and without limitation by an electroencephalogram (EEG)), eye movement or levels of relaxation (detected, for example and without limitation by an electromyography (EMG)), and/or acceleration of the user to determine the effectiveness of the device and method and then modify the stimulus to achieve desired results. Thus, for example, if a user is using the device or method to relax and the biosensor indicates that a user has reached a relax state, then the device or method is programmed to reduce the intensity and/or time of the stimulus, or to favor certain types of stimulus.

In certain embodiments, the sensory stimulation is tailored to the user based on the biological response of the individual in real time. Thus, for example and without limitation, measurements of heart rate, brain activity, temperature, and/or indications of stress levels or sleep may be obtained and used to modify the time, intensity, and/or pattern of stimuli provided to a person.

Examples of neurological disorders which may be treated with devices and methods may include, but are not limited to, insomnia, post-traumatic stress disorder (PTSD), brain injuries including, but not limited to traumatic brain injury (TBI), mild traumatic brain injury (mTBI), or injury from oxygen deprivation of the brain from strokes, depression, anxiety, mood disorders, personality disorders, eating disorders, psychotic disorders, and balance disorders. Alternatively, or in combination, the stimulus provided by the medical devices and methods described herein may provide cognitive benefits and/or enhancement, including, but not limited to, improving neuroplasticity, motor skills, coordination, reaction times, alertness, energy, working memory, mood, relaxation, improved sleep (latency and or quality) and feelings of wellbeing.

In certain embodiments, stimuli may be provided to the wearer of a headset or sleep mask that may be comfortably worn by a user, such as in bed to induce sleep. The wearable headset or sleep mask may be operated by a personal computing device of the user, such as smartphone, having downloaded and active thereon a control application or "app" for the therapy. The wearable headset or sleep mask may also concurrently provide tactile stimuli, and the tactile stimuli may be provided from bone conduction transducer that may concurrently provide the auditory stimuli. Various patterns of the stimuli to induce different user responses are also disclosed. Certain embodiments thus alter, in real time, stimulus to the user based on the response of the individual using one or more sensors mounted within the headset sensing biological signals, including but not limited to heart rate, heart rate variability, temperature, motion, galvanic skin response, eye movement or state of relaxation using EMG and EEG. The sensor measures the response of the individual to the stimulus and alters the patterns accordingly.

The primary ways by which the stimulus can be optimally altered using the sensor data includes, but are not limited to, changing the volume of the auditory stimulation and brightness of the visual stimulation in response to the change in level of relaxation or arousal of the subject, and/or shortening or lengthening the duration of each of the sections in the patterns disclosed.

In certain embodiments, a device is provided that produces an output that may be perceived by a user of the device as a visual, auditory or tactile stimulus at one or more frequencies, or in one or more frequency ranges. This is augmented to include a sensor providing changes to the stimulus. In certain embodiments, the stimuli may be turned on and off at frequencies that are believed to induce one or more frequencies of electrical activity in the brain, which are generally accepted as being delta waves (1.0 to 3.0 Hz), theta waves (3.0 to 7.0 Hz), alpha waves (7.0 to 12 Hz), beta waves (12 to 38 Hz), and gamma waves (38 to 42 Hz).

Thus, for example, one embodiment device produces an output that may be perceived by a user of the device as a stimulus at sequential frequencies, such as sequences of alpha waves, theta waves, and delta waves. In certain embodiments, the stimuli are a coordinated auditory and visual stimulation, providing right and left eyes and ears to pulsed light and pulsed auditory in each of the ranges listed above. As one example, the coordinated stimulation may be: 1) both eyes and both ears being stimulated at the same time; 2) the left eye and ear being stimulated at the same time, followed by the right eye and ear being stimulated at the same time; 3) both eyes being stimulated at the same time, followed by both ears being stimulated at the same time; or 4) the right eye and left ear being stimulated at the same time, followed by the left eye and right eye being stimulated at the same time. In each case, the stimulation may include, for example, sequentially stimulating in the alpha wave range, followed by the theta wave range, followed by the delta wave range. The stimulation can last for a period of one minute up to an hour.

It is one aspect to provide a method of providing stimulation to a user for a treatment time. The method includes: providing a headset to be worn by the user, where the headset includes four stimuli sources including a left light source activated to provide visual stimuli to the left eye of the user, a right light source activated to provide visual stimuli to the right eye of the user, a left vibration source activated to provide auditory stimuli to the left side of a head of the user, and a right vibration source activated to provide auditory stimuli to the right side of the head of the user; obtaining a measurement of the user using a sensor; determining a state of the user from the obtained measurement; activating each of the stimuli sources between a high stimuli and a low stimuli at a stimulation frequency for a period of time including, where at least part of the activating includes activating at least two of the four stimuli sources out of phase with the activating of at least two other of the four stimuli sources; and modifying the activating according to the determined state of the user. In one embodiment, the activating further includes synchronously activating the four stimuli sources for a period of time.

In another embodiment, the activating includes one or more of: synchronously activating the left light source and the left vibration source out of phase with the right light source and the right vibration source for a period of time, synchronously activating the left light source and the right light source out of phase with the left vibration source and the right vibration source for a period of time, or synchronously activating the left light source and the right vibration source out of phase with the left vibration source and the right light source for a period of time.

In yet another embodiment, the activating includes alternating between: synchronously activating the four stimuli sources for a period of time, synchronously activating the left light source and the left vibration source out of phase with the right light source and the right vibration source for a period of time, synchronously activating the left light source and the right light source out of phase with the left vibration source and the right vibration source for a period of time, and synchronously activating the left light source and the right vibration source out of phase with the left vibration source and the right light source for a period of time.

In one embodiment, modifying includes modifying the stimulation frequency of the four stimuli sources. In another embodiment, the modifying includes modifying the temporal length of the activating of the four stimuli sources. In yet another embodiment, the modifying includes modifying a high stimuli level of at least one stimuli source of the four stimuli sources. In one embodiment, the modifying includes modifying the temporal length of the activating of the four stimuli sources.

In one embodiment, the sensor is a heart rate sensor, a heart rate variability (HRV) sensor, a temperature sensor, a motion sensor, a galvanic skin response sensor, an accelerometer, an EEG or an EMG. In one embodiment, the determined state of the user is a state of sleep or the level or change in level of relaxation or arousal.

In another embodiment, the modifying includes modifying a high stimuli level of the left vibration source and the right vibration source. In one embodiment, the modifying includes modifying a high stimuli level of the left light source and the right light source. In yet another embodiment, the activating according to the determined state of the user includes modifying the temporal length of the activating of the four stimuli sources.

In one embodiment, the activating includes activating each of the stimuli sources at a first stimulation frequency for a first period of time and activating each of the stimuli sources at a second stimulation frequency for a second period of time, where the first stimulation frequency is in a first frequency range of 1.0 and 3.0 Hz, 3.0 to 7.0 Hz, 7.0 to 12 Hz, 12 to 38 Hz or 38 to 42 Hz, and where the second stimulation frequency is in a second frequency range of 1.0 and 3.0 Hz, 3.0 to 7.0 Hz, 7.0 to 12 Hz, 12 to 38 Hz or 38 to 42 Hz, and where the first stimulation frequency is in a different frequency range than the second stimulation frequency range.

In one embodiment, the determined state of the user is a state of sleep determined to be REM sleep, the where the modifying the activating according to the determined state of the user includes reducing the high stimuli level at least one of the four stimuli sources. In another embodiment, the sensor is a temperature sensor, an EMG sensor, a heart rate sensor, an HRV sensor, and EEG sensor, or an accelerometer. In yet another embodiment, the sensor is two or more sensors including a first sensor including one of an HRV sensor or a heart rate sensor and one or more sensors including a temperature sensor, an EMG sensor, an EEG sensor, or an accelerometer. In one embodiment, the modifying the activating according to the determined state of the user includes reducing the stimuli level of each of four stimuli sources until the stimuli sources are turned off.

In one embodiment, the sensor is a heart rate sensor or a heart rate variability (HRV) sensor, where the determined state of the user is a state of relaxation or sleep state indicated by the HRV. In another embodiment, the determined state of the user is a state of relaxation or sleep state indicated by an increase in HRV, and where the modifying the activating according to the determined state of the user includes reducing the stimuli level of each of four stimuli sources until the stimuli sources are turned off and/or shortening the treatment time. In yet another embodiment, the determined state of the user is a less relaxed state or stressed state indicated by a decrease in HRV, and where the modifying the activating according to the determined state of the user includes increasing the stimuli level of each of four stimuli sources and/or increasing the treatment time.

In one embodiment, the determined state of the user is a hemispheric imbalance of brainwaves, where the sensor is an EEG sensor, where the state is the hemispheric imbalance of brainwaves includes a more active hemisphere of the brain, and where the modifying the activating according to the determined state of the user includes increasing the high stimuli level stimuli sources to the less active hemisphere of the brain.

One embodiment is a device to provide stimulation to a user for a treatment time. The device includes: a headset to be worn by the user, where the headset includes four stimuli sources including a left light source activated to provide visual stimuli to the left eye of the user, a right light source activated to provide visual stimuli to the right eye of the user, a left vibration source activated to provide auditory stimuli to the left side of a head of the user, and a right vibration source activated to provide auditory stimuli to the right side of the head of the user, a sensor in to obtain a measurement of the user; and a processor. The processor is programmed to accept the measurement and determine a state of the user from the measurement, determine a state of the user from the obtained measurement, activate each of the stimuli sources between a high stimuli and a low stimuli at a stimulation frequency for a period of time including, where at least part of the activating includes activating at least two of the four stimuli sources out of phase with the activating of at least two other of the four stimuli sources, and modify the activation of each of the stimuli sources according to the state of the user.

In one embodiment, the sensor includes one or more of a heart rate sensor, a heart rate variability (HRV) sensor, a temperature sensor, a motion sensor, a galvanic skin response sensor, an accelerometer, an EEG or an EMG. In another embodiment, the processor is programmed to further activate the four stimuli sources synchronously for a period of time. In yet another embodiment, the processor is programmed to alternate between synchronously activating the four stimuli sources for a period of time, synchronously activating the left light source and the left vibration source out of phase with the right light source and the right vibration source for a period of time, synchronously activating the left light source and the right light source out of phase with the left vibration source and the right vibration source for a period of time, and synchronously activating the left light source and the right vibration source out of phase with the left vibration source and the right light source for a period of time.

In one embodiment, the state of the user is a state of sleep or the level or change in level of relaxation or arousal determined from a temperature sensor, a heart rate or HRV sensor. In yet another embodiment, the processor is programmed to modify the activation of each of the stimuli sources according to the state of the user includes one or more of changing the high stimuli level at least one of the four stimuli sources, the stimulation frequency, or the treatment time.

In one embodiment, the state of the user is a state of hemispheric imbalance of brainwaves, where the sensor is an EEG sensor, where processor is programmed to increase the high stimuli level stimuli sources to the less active hemisphere of the brain.

These features together with the various ancillary provisions and features which will become apparent to those skilled in the art from the following detailed description, are attained by the methods and system for providing stimulation to a user of the present invention, embodiments thereof being shown with reference to the accompanying drawings, by way of example only, wherein:

DETAILED DESCRIPTION OF THE INVENTION

Figure 1A:
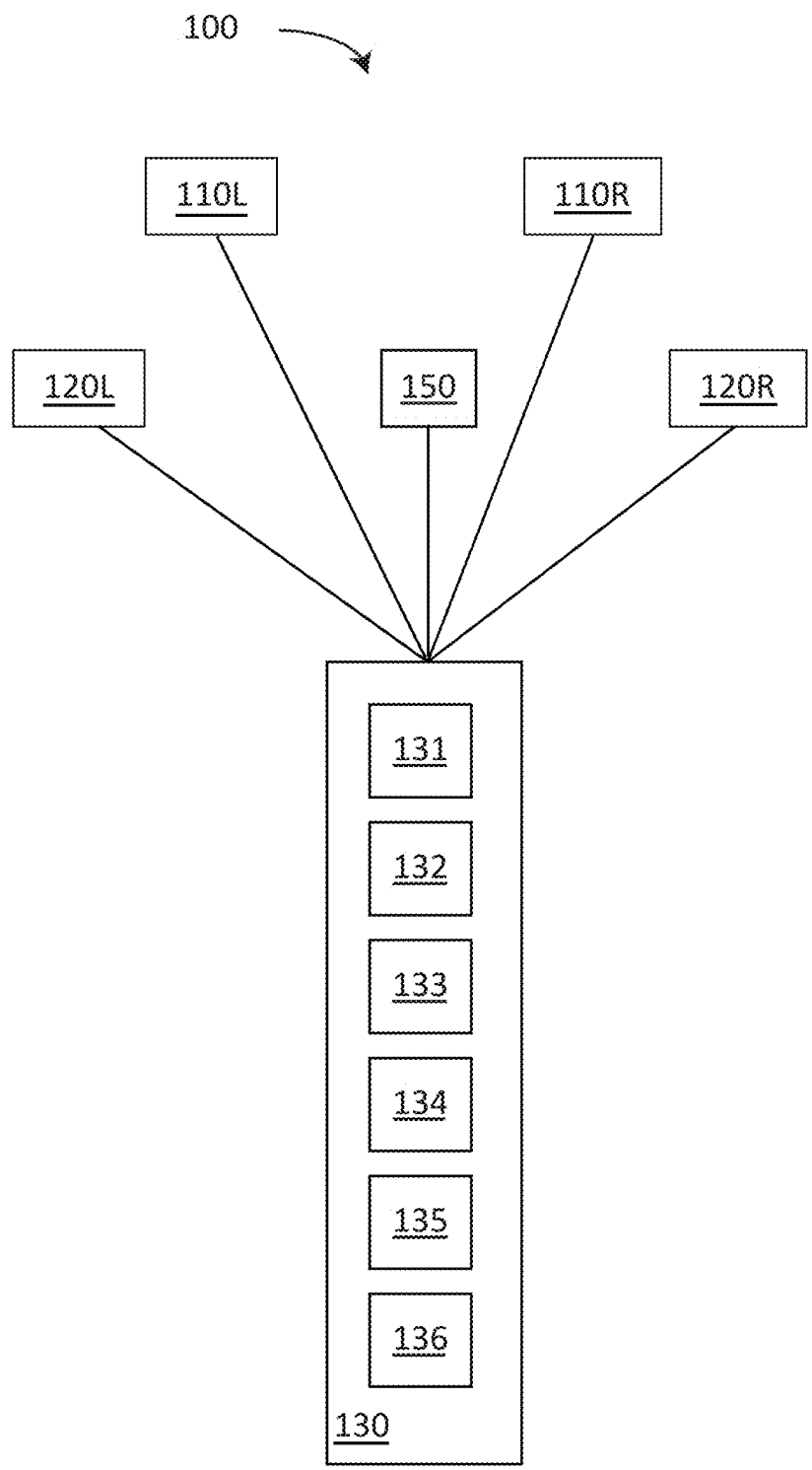
FIGS. 1A and 1B show schematic diagrams of therapeutic systems to provide therapeutic auditory, visual, and/or tactile stimulus to the user.

FIG. 1A is a schematic diagram of a first embodiment therapeutic system 100. Therapeutic system 100 provides one or more outputs that a person wearing the therapeutic system may experience as auditory, visual, and/or tactile stimulus. Thus, in one embodiment, therapeutic system may comprise a left light source 110L, a right light source 110R, a left vibration source 120L, a right vibration source 120R, and a controller 130 for independently controlling and coordinating the action of the light and vibration sources. Thus, for example, therapeutic system 100 may be positioned on the head of a user with left light source 110L positioned over the left eye to provide a left visual stimulus, right light source 110R positioned over the right eye to provide a right visual stimulus, left vibration source 120L positioned to provide left ear auditory stimuli, and right vibration source 120R positioned to provide right ear auditory stimuli.

In one embodiment, left and right light sources 110L, 110R may each comprise light-emitting diodes, an incandescent light source having a wavelength filter, a fluorescent light source, a backlit LCD panel, or other light source configured to provide to the user light at a desired, predetermined wavelength or wavelength range.

In certain embodiments, left and right light sources 110L, 110R are separately controlled to provide output at a stimulation frequency comprising alternating between a high stimuli, where the light sources are activated (or "on") and where the light sources have a lower, or no activation (both referred to herein as being "off"). The alternating may, for example and without limitation, be in the form of a square wave, a triangular shape wave, a sine wave, or some other waveform.

The alternating may, for example and without limitation, be in the form of a square wave, a triangular shape wave, a sine wave, or some other waveform.

Thus, for example and without limitation, a light source may be programmed to provide an output of light that alternates between a high light level (a high stimuli) and a lower light level (a low stimuli) at a rate, or stimulation frequency of between 1.0 and 42 Hz.

In one embodiment, left and right vibration sources 120L, 120R may each comprise earbuds, miniature speakers, or other vibration sources that can provide auditory stimuli to a user. In certain other embodiments, left and right vibration sources 120L, 120R may comprise bone conduction transducers in the audible frequency range to provide vibrations to the user's skull bone that is sensed as auditory by the user's ear. Optionally, one or more of left and right vibration sources 120L, 120R may also produce vibrations that are sensed as tactile stimuli. Thus, for example, controller 130 may provide first signals to bone conduction transducers that vibrate or oscillate at a first frequency that can be interpreted by the user as auditory stimuli and may provide second signals at a second, lower frequency that can be interpreted as a tactile sensation by the user. In other words, bone conduction transducers may be adapted to provide both auditory and tactile stimulus to the user.

In certain embodiments, left and right vibration sources 120L, 120R provide output at specific one or more frequencies or a range of frequencies. In one embodiment, left and right vibration sources 120L, 120R are separately controlled to provide output at a stimulation frequency comprising alternating between a high stimuli, where the vibration sources are activated (or "on") and where the vibration sources have a lower, or no activation (or "off"). In certain embodiments, left and right light sources 110L, 110R are separately controlled to provide output at a stimulation frequency comprising alternating between a high stimuli, where the light sources are activated (or "on") and where the light sources have a lower activation, or no activation (both referred to herein as being "off"). The alternating may, for example and without limitation, be in the form of a square wave, a triangular shape wave, a sine wave, or some other waveform.

In one embodiment, the intensity of the high and low stimuli of light and vibration, the stimulation frequency, and the time over which the stimulation is provided are controlled by controller 130 in differing stimulation patterns. The stimulation patterns may include, but are not limited to: 1) all of the stimuli being synchronous (the high and low stimuli occurring at the same time): or 2) pairs of stimuli being synchronous and out of phase with other pairs of stimuli. Examples of pairs of stimuli being synchronous and out of phase with other pairs of stimuli include: a) the first pair being left side light and vibration and the second pair being right side light and vibration; b) the first pair being left side light and right side light and the second pair being right side vibration and left side vibration; and c) the first pair being left side light and right side vibration and the second pair being right side vibration and left side light.

In one embodiment, the intensity of the high and low vibration and light stimuli, the stimulation frequency, and the time over which the stimulation is provided are controlled by controller 130.

Thus, for example and without limitation, a vibration source may be programmed to provide an output at an audio frequency of 256 Hz that alternates between a high vibration level (a high stimuli) and a lower vibration level (a low stimuli) at a rate, or stimulation frequency of between 1.0 and 42 Hz. Thus, in this example, the vibration source is the product of an audio frequency and a square wave.

Therapeutic system 100 also includes a sensor assembly 150 that obtains one or more measurements from the user of the therapeutic system. Thus, for example and without limitation, sensor assembly 150 may include, or is in communication with, a sensor that measures some property or characteristic of the user, including but not limited to, heart rate, heart rate variability, body temperature, or blood pressure, and includes electronics that provide a signal indicative of the measurement to controller 130. In other embodiments, one or more sensors are connected to sensor assembly 150 by wired or wireless connectors. Thus, in various embodiments, the sensors may include one or more: electrodes for sensing electrical activity in the brain, as in a 2 or 4 lead EEG, a temperature sensor, and/or a heartbeat sensor, or one or more EMG sensors positioned, for example and without limitation, to measure eye movement to ascertain when REM sleep is reached, and/or to measure muscle tone to aid in determining states of relaxation. Controller 130 may utilize the signal from sensor assembly 150 to modify the intensity and/or timing of the light and vibration sources.

In one embodiment controller 130 includes: an output 131 to provide signals to actuate light sources 110L and 110R, vibration sources 120L and 120R, and any other components that provide sensory input to the user; an input 132 to accept signals from sensor assembly 150; a non-transitory memory 133 for storing programming and data for system 100; a processor 134; and a communications module 135. Memory 133 includes instructions that are accessible to processor 134 for operating the components that provide sensory input to the user, including but not limited to light sources 110L and 110R, vibration sources 120L and 120R, including accepting input provided to input 132 and modifying signals provided to components that provide sensory input to the user, including but not limited to light sources 110L and 110R, vibration sources 120L and 120R. Communications module 135 provides for the transfer of information to or from controller 130 by wired or wireless means.

Figure 1B:
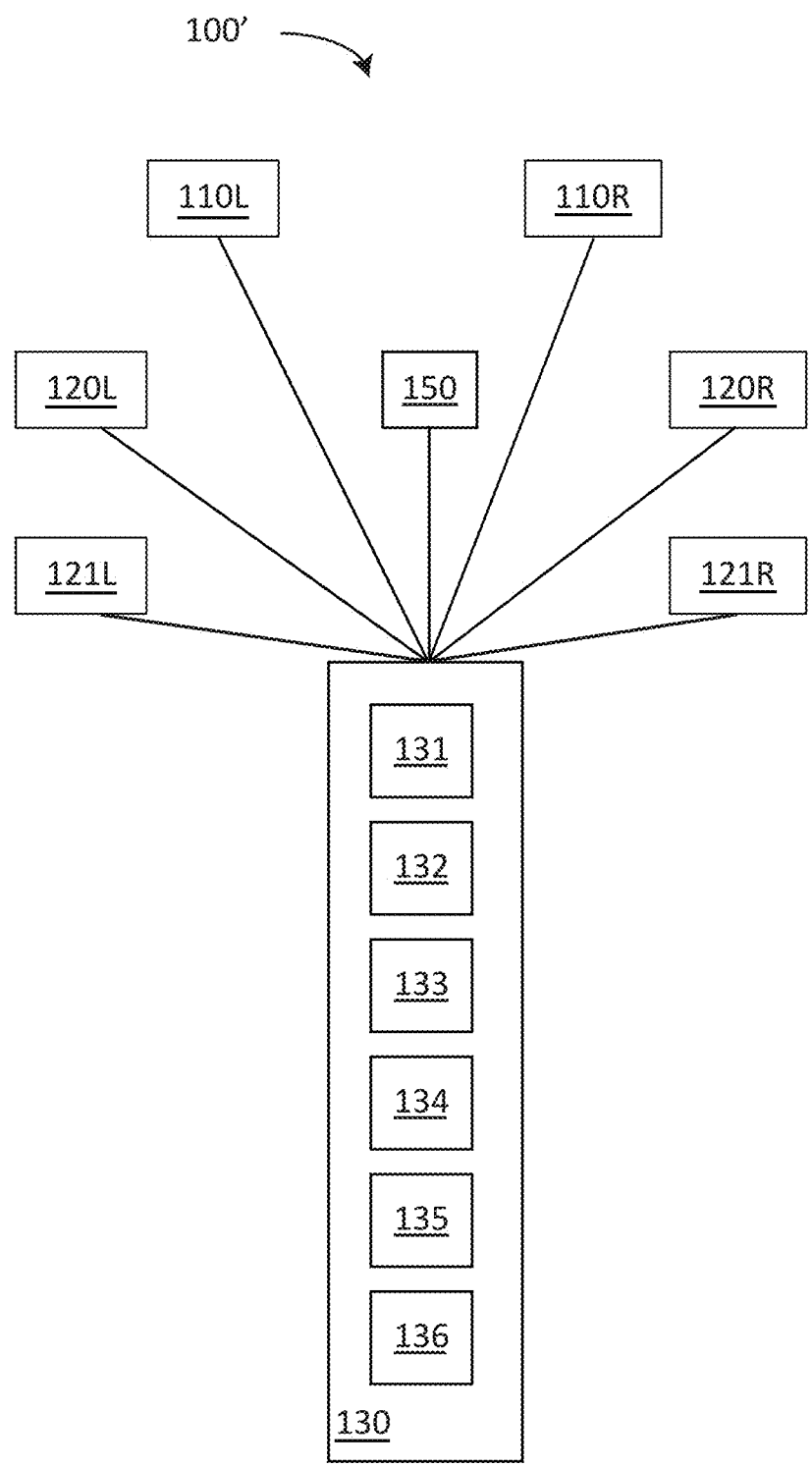

FIG. 1B is a schematic diagram of a second embodiment therapeutic system 100'. Second embodiment therapeutic system 100' is generally similar to first embodiment therapeutic system 100, except as explicitly noted. Specifically, second embodiment therapeutic system 100' includes a left tactile stimulus source 121L and a right tactile stimulus source 121R, each of which may be individually controlled and coordinated with the controller 130 to provide tactile stimuli to a user of therapeutic system 100'.

Figure 2A:
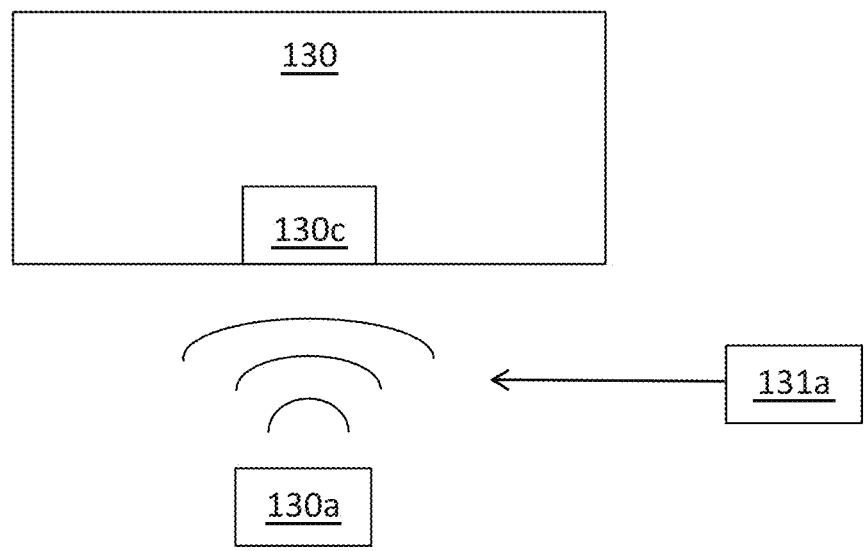
FIGS. 2A and 2B show schematic diagrams of the controller for the therapeutic systems of FIGS. 1A and 1B.
Figure 2B:
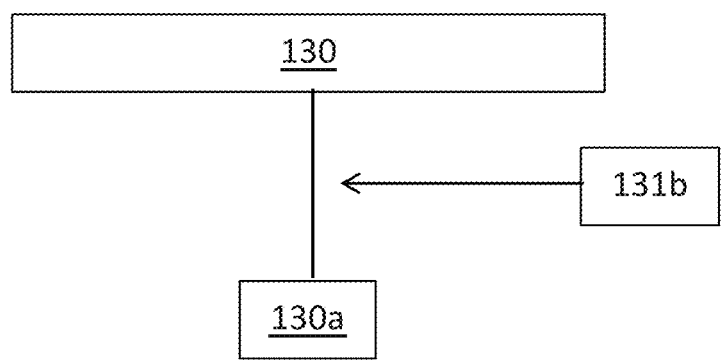

FIGS. 2A and 2B show schematic diagrams of the controller 130 of therapeutic system 100 or 100'. As shown in FIG. 2A, therapeutic system 100 or 100' may optionally include an external control unit 130a that may wirelessly communicate with a wireless receiver/transmitter 130c of the controller 130 through a wireless connection 131a. The wireless connection 131a may comprise a Bluetooth connection, a Bluetooth LE connection, a WiFi connection, a ZigBee connection, an infrared (IR) connection, a radiofrequency (RF) connection, or an inaudible auditory signal connection, to name a few examples. The external control unit 130a may comprise a custom-built, electronic controller. In many embodiments, the external control unit 130a may comprise a personal computing device of the user that may have downloaded onto and operating, a custom computer application or "app" to operate the system 100 or 100' to provide a therapeutic regimen. For example, the personal computing device may comprise a personal computer, a personal laptop computer, a tablet computer (such as an Apple iPad, a Samsung Galaxy Tab, a Microsoft Surface, or an Amazon Fire, to name a few examples), a smartphone (such as an Apple iPhone, a Samsung Galaxy phone, or a Google Nexus phone, to name a few examples), and the custom computer application or "app" may be an application or "app" downloadable from an application distribution platform such as Apple iTunes, Apple Store, Google Play, Google Chrome Web Store, Amazon App Store, or Microsoft Windows Store, to name a few examples. The application may include one or more therapeutic regimens that the user may select for implementation by the therapeutic system 100 or 100'. In some embodiments, the application may allow the user to provide feedback information about the efficacy of the therapeutic regimen(s), the feedback may be uploaded and collected by a central server(s) in communication with the application, and the therapeutic regimen(s) may be improved or optimized based on the feedback from the one or more users. Alternatively, or in combination, as shown in FIG. 2B, the system 100 or 100' may further comprise an external control unit 130a, such as a custom-built controller, that may communicate with the controller 130 through a wired connection 131a, for example, a USB, FireWire, or Lightning connection, to name a few examples.

Figure 3A:
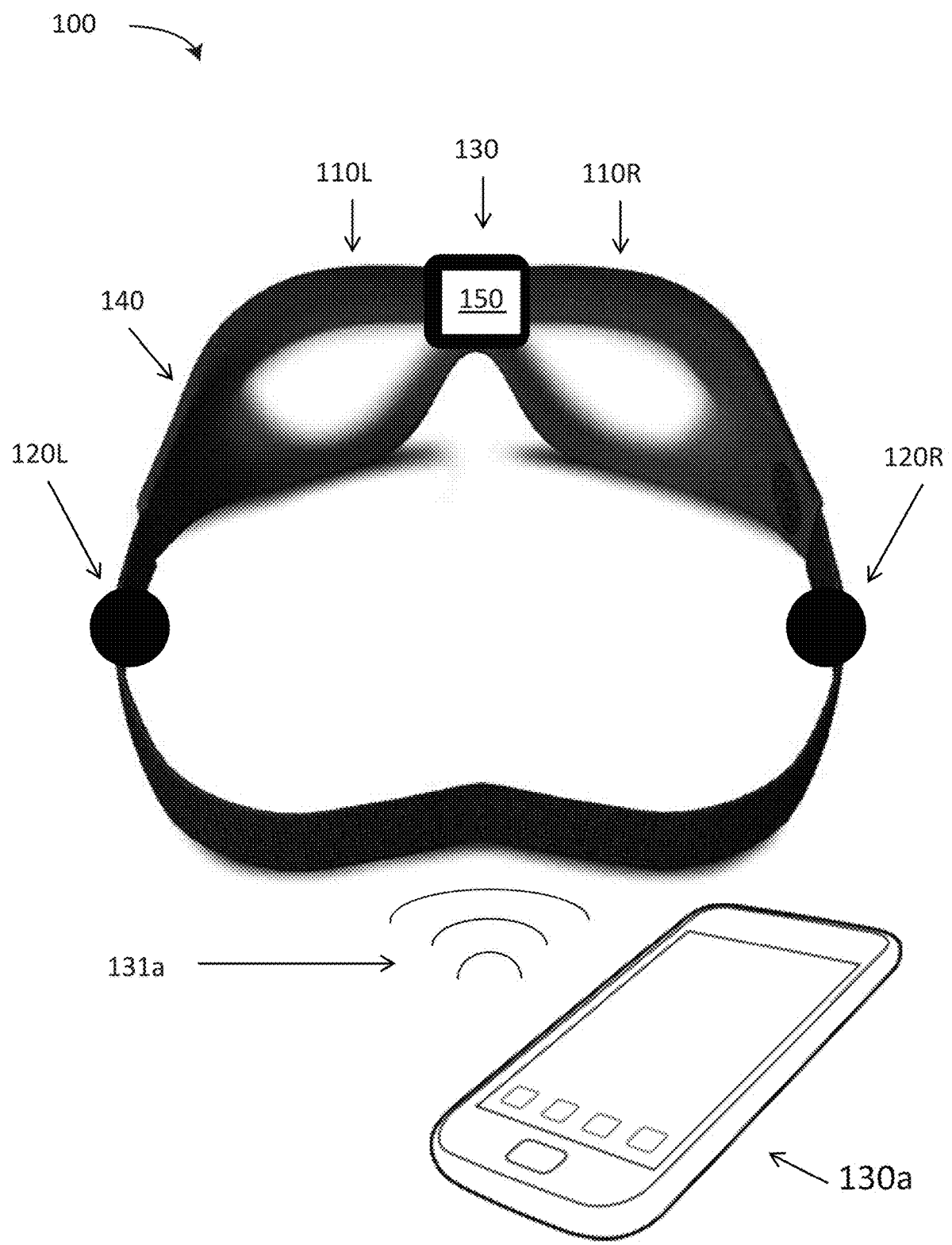
FIG. 3A shows a first embodiment therapeutic wearable headset or sleep mask.

FIG. 3A shows one embodiment of therapeutic system 100 as including a first embodiment therapeutic wearable headset or sleep mask 140 which integrates the light, vibration, and, optionally, tactile sources into a single form factor for presentation to a user. Thus, for example, when a user places wearable headset or sleep mask 140 on their head, left light source 110L is positioned over the left eye to provide a left visual stimulus, right light source 110R is positioned over the right eye to provide a right visual stimulus, left vibration source 120L is positioned to provide left ear auditory stimuli, and right vibration source 120R is positioned to provide right ear auditory stimuli.

As discussed above and herein, the left vibration source 120L and the right vibration source 120R may each comprise bone conduction transducer that may provide both auditory and tactile stimulus. Alternatively, wearable headset or sleep mask 140 is therapeutic system 100' which includes left tactile stimulus source 121L and right tactile stimulus source 121R, each of which may be individually controlled and coordinated with the controller 130, as described above regarding FIG. 1B.

Figure 3B:
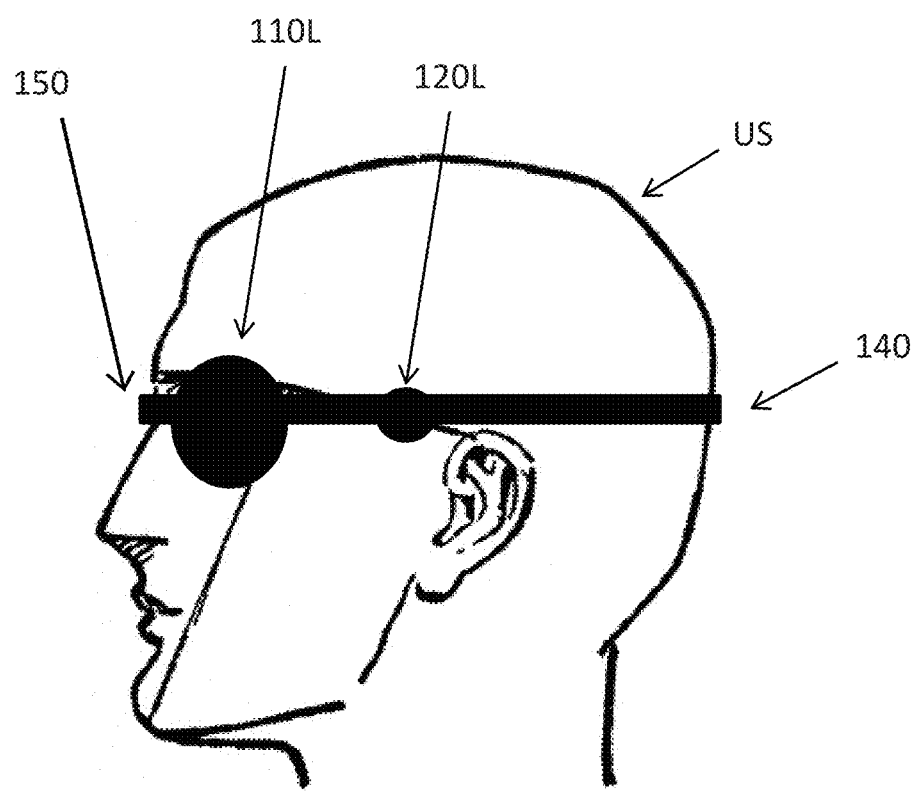
FIG. 3B shows a user wearing the therapeutic wearable headset and sleep mask of FIG. 3A.

As discussed above and herein, the therapeutic wearable headset or sleep mask 140 may be operated with an external controller 130a (e.g., a smartphone) in communication with the controller 130 through a wireless connection 131a, for example. The user US may have an option to turn tactile stimulation on or off, for example. FIG. 3B shows a user US wearing the therapeutic wearable headset or sleep mask 140.

Figure 5:
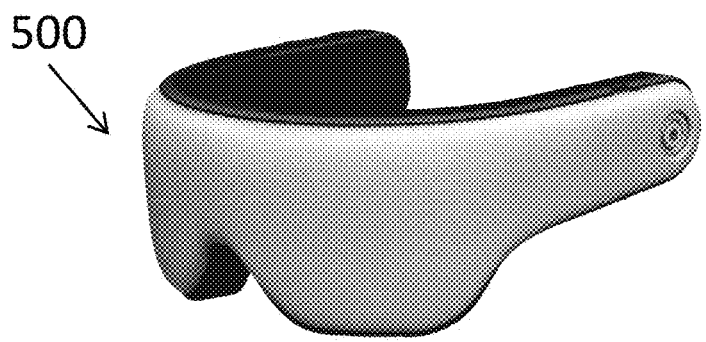
FIG. 5 is a front right perspective view of a second embodiment therapeutic wearable headset or sleep mask.
Figure 6:
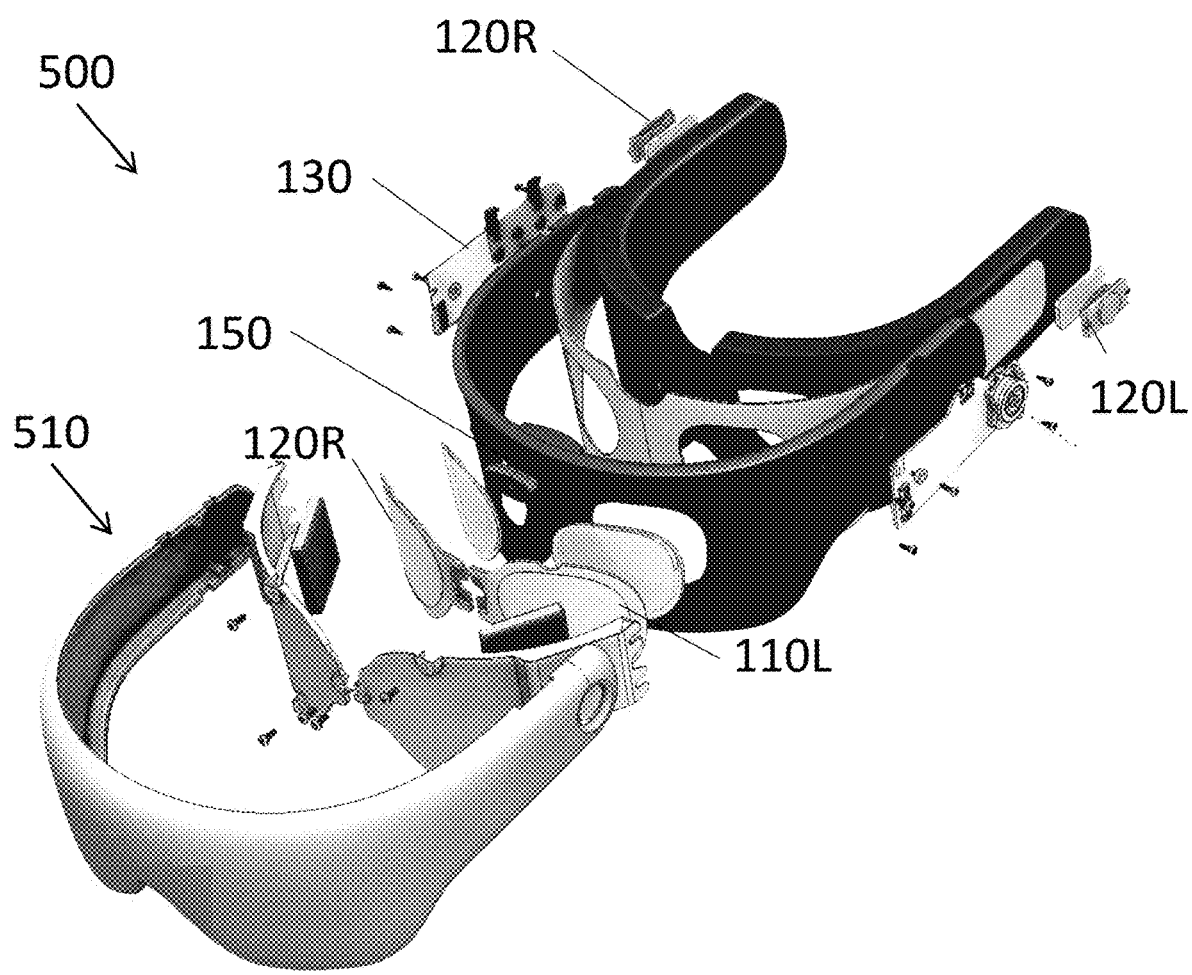
FIG. 6 is a top right exploded view of the therapeutic wearable headset or sleep mask of FIG. 5.

FIG. 5 is a front right perspective view and FIG. 6 is a top right exploded view of a second embodiment therapeutic wearable headset or sleep mask 500. Headset 500 is generally similar to headset 140, except as explicitly stated.

As shown in FIGS. 5 and 6, headset 500 includes a cover 510, sensor assembly 150, controller 130, light sources 110L and 110R, and vibration sources 120L and 120R. Sensor assembly 150 may include a biometric sensor system, such as that which is sold under the name of VALENCELL BENCHMARK™ (Raleigh, N.C.), that includes an infrared light source and detector, which can be used to detect heart rate using pulse oximetry, an accelerator, and a processing unit. Sensor assembly 150 includes a sensor module circuit board that contains a digital optical detector system. This detector controls the LEDs and converts the optical signals reflected from the user's skin to digital format and communicates over the internal I2C bus to the PerformTek® processor. The accelerometer is also read via the internal I2C bus for activity signal.

Controller 130 may include, for example and without limitation, a Nordic Semiconductor ASA (Oslo, Norway) model NRF51822 Multiprotocol BLUETOOTH® low energy/2.4 GHz RF System on Chip, and a VLSI Solution (Tampere, Finland) model VS1000 audio module.

Light sources 110L and 110R may include, for example and without limitation, Lite-On, Inc. (Milpitas, Calif.) Bin G3/W2/AU model LTST-020VSKT LEDS. Vibration sources 120L and 120R are Basen Technology Co, Ltd model PN: OEM-E170a earbuds.

Sensor assembly 150 may include, for example and without limitation, a PerformTek® processor which polls sensor data over the internal I2C bus and converts the raw measurements into data registers of biometric values (i.e. Heart Rate, Cadence, VO2) and processes those values further into higher level user assessments (i.e. Calories Burned, Distance, VO2 max, fitness level, and the period between heart rate beats (the Heart Rate Interval, or RR Interval)). The PerformTek® processor runs algorithms to convert the raw signals to a register array of biometric values and high-level assessments. These values are available for reading via the UART or I2C firmware interface. In addition, sensor module diagnostics such as signal quality, error codes, and serial number ID are available.

Sensor assembly 150 further includes control lines for interfacing controller 130 with the PerformTek® processor include a Power On Self-Test (POST), UART or I2C communication interface, and a wake-from-standby line (WAKE). The host processor can control much of the functionality of the sensor module via a software protocol interface over the UART or I2C interface.

In one embodiment, sensor assembly 150 determines a current Heart Rate, which is provided to controller 130. In another embodiment, sensor assembly 150 also provides accelerometer data to controller 130.

In yet another embodiment, sensor assembly 150 includes one or more EEG sensors, as are known in the field, and provides brain electrical activity measurements to controller 130.

In another embodiment, sensor assembly 150 includes one or more EMG sensors positioned, for example and without limitation, to measure eye movement to ascertain when REM sleep is reached, and/or to measure muscle tone to aid in determining states of relaxation. EMG sensors, as are known in the field, and provides brain electrical activity measurements to controller 130.

Figure 7A:
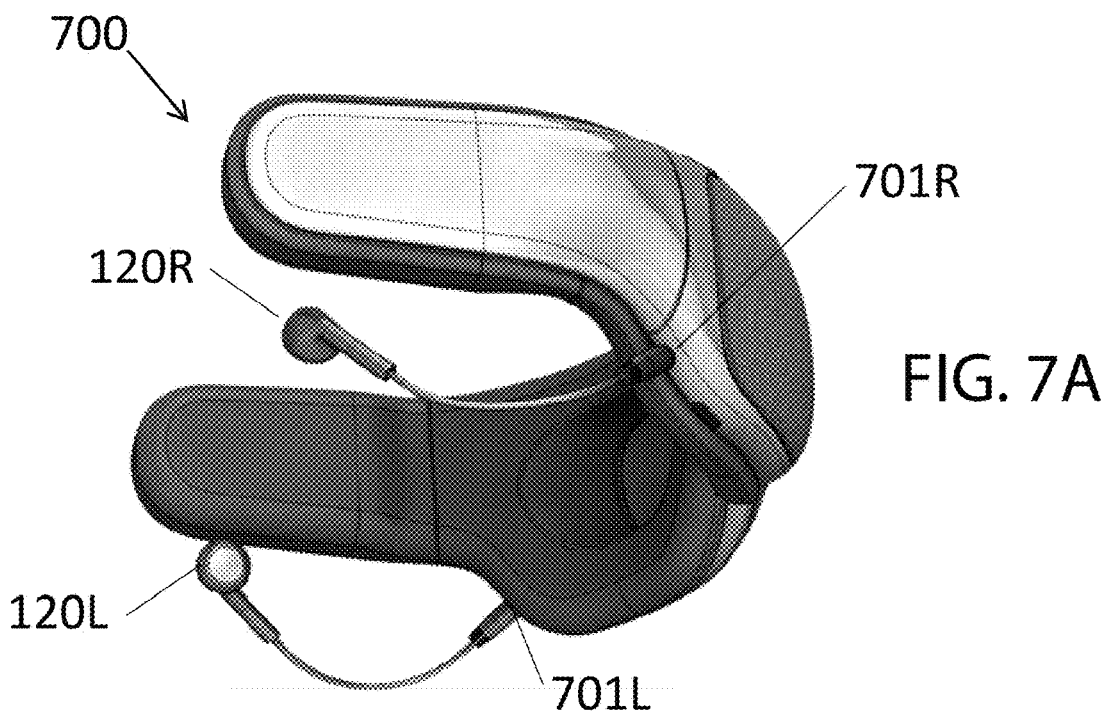
FIGS. 7A, 7B, and 7C are a bottom right perspective view, a rear view, and a left view, respectively, of a third embodiment therapeutic wearable headset or sleep mask.
Figure 7B:
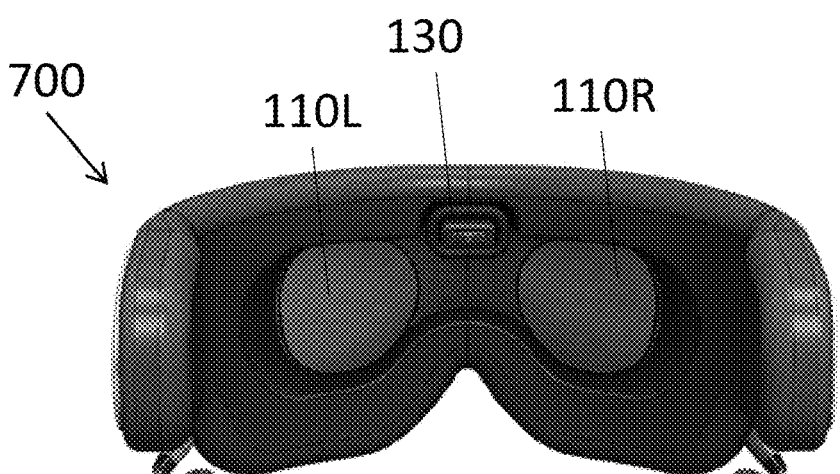
Figure 7C:
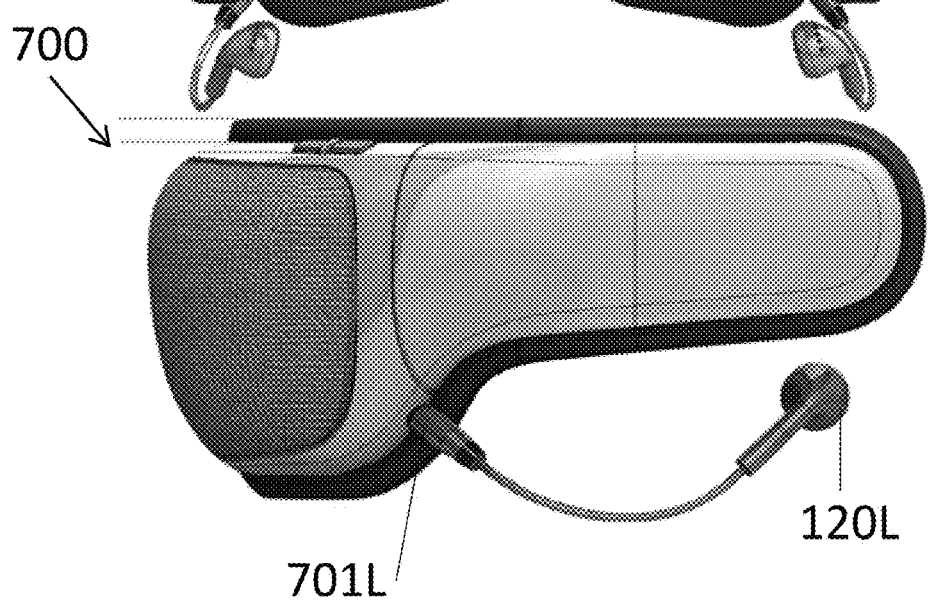
Figure 8:
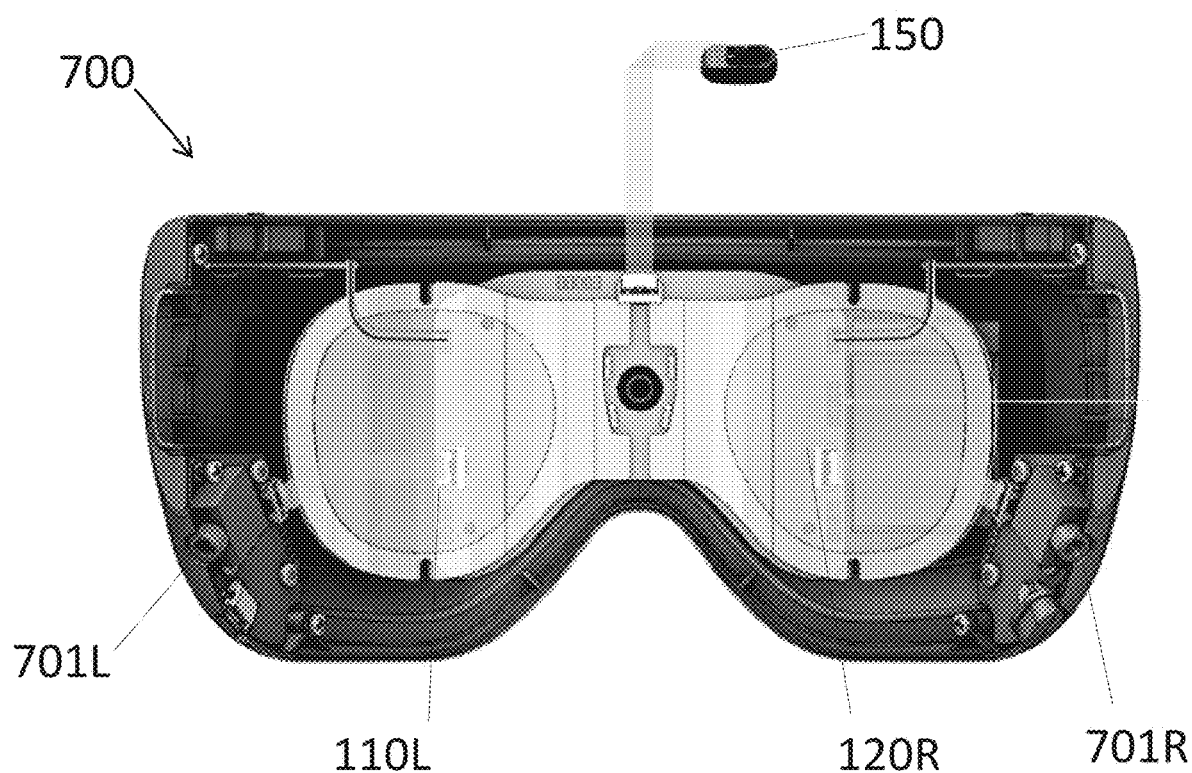
FIG. 8 is an exploded front view of the embodiment of FIG. 7A.

FIGS. 7A, 7B, and 7C are a bottom right perspective view, a rear view, and a left view, respectively, and FIG. 8 is an exploded front view of a third embodiment therapeutic wearable headset or sleep mask 700. Headset 700 is generally similar to headset 500, except as explicitly stated.

Headset 700 differs from headset 500 in that headset 700 includes left and right audio jacks 701L and 701R into which left and right earbuds 120L and 120R, respectively, may be plugged into. Alternatively, stereo headphones (not shown) may be plugged into one of jacks 701L or 701R, where the jacks are appropriately programmed to provide stereo sound to the headphones.

Figure 4:
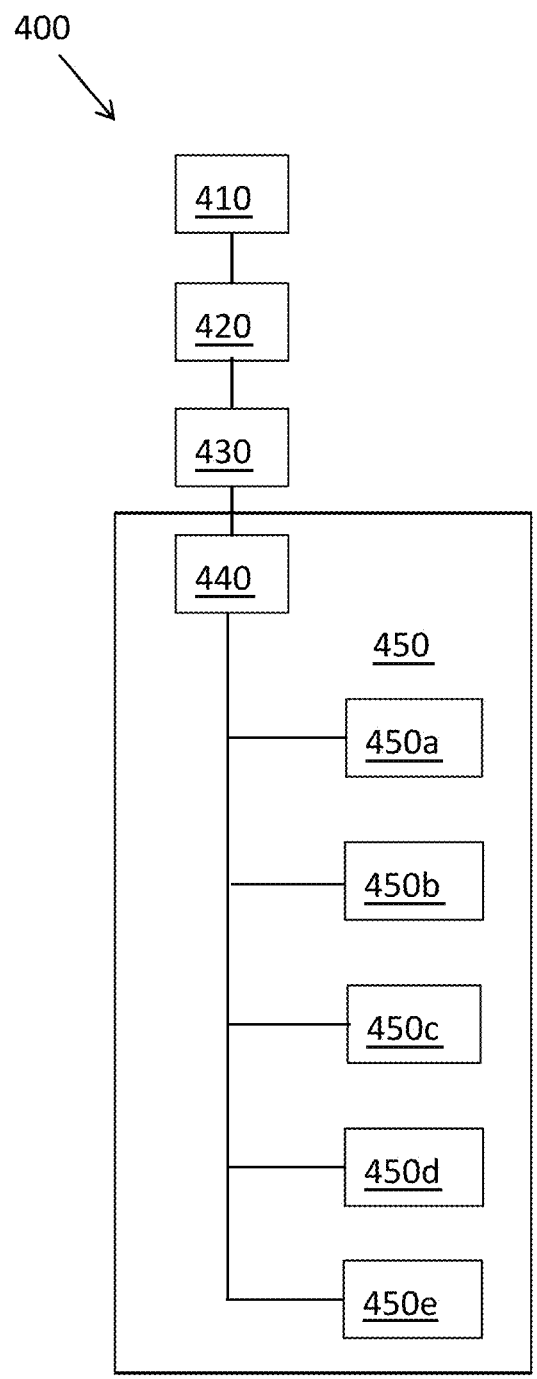
FIG. 4 shows a flow chart of a therapeutic method of providing therapeutic auditory, visual, and/or tactile stimulus, according to several embodiments.

FIG. 4 shows a flow chart of an exemplary therapeutic method 400 for providing therapeutic auditory, visual, and/or tactile stimulus. In a step 410, a subject having a neurological disorder or condition may be identified. Examples of neurological disorders may include, but are not limited to, insomnia, post-traumatic stress disorder (PTSD), brain injuries such as traumatic brain injury (TBI), mild traumatic brain injury (mTBI), or injuries to the brain due to oxygen deprivation, such as strokes, depression, anxiety, mood disorders, personality disorders, eating disorders, and psychotic disorders. Alternatively, a subject may be selected to undergo a therapeutic method 400 for the purpose of performance enhancement of mental and/or physical tasks for to aid the subject in napping or sleeping. In a step 420, the subject may be provided the therapeutic system or headwear, such as the system 100 or 100' described above. In a step 430, the subject may wear the therapeutic system or headwear, such as wearable headset or sleep mask 140, 500, or 700. In a step 440, headset 140 executes programming 450 provided in controller 130 to provide stimuli to the subject. The programming provides two or more of auditory, visual, and/or tactile stimulus are concurrently provided by headset 140 to the subject, and thus, for example, may provide power to activate left light source 110L, right light source 110R, left vibration source 120L and or right vibration source 120R. The programming also includes modifying the auditory, visual, and/or stimuli in response to measurements obtained by sensor assembly 150 and provided to controller 130.

As discussed above and herein, the left vibration source 120L and the right vibration source 120R may each comprise bone conduction transducer that may provide both auditory and tactile stimulus. Alternatively, wearable headset or sleep mask 140 500, or 700 is therapeutic system 100' which includes left tactile stimulus source 121L and right tactile stimulus source 121R, each of which may be individually controlled and coordinated with the controller 130, as described above regarding FIG. 1B.

In certain embodiments, providing two or more of auditory, visual, and/or tactile stimulus concurrently may provide improved therapeutic benefits as compared to providing only one of auditory, visual, or tactile stimulus at one time. The two or more auditory, visual, and/or tactile stimulus may thus combine to provide the improved therapeutic benefits, for example (i.e., the two or more auditory, visual, and/or tactile stimulus may synergize in a way to provide improved results over providing two of the stimuli individually.)

Exemplary instructions for providing stimuli may be provided, for example, by programming 450, which includes one or more subroutines. One such subroutine is subroutine 450e, which analyzes measurements obtained from sensor assembly 150 and stores the analyzed measurements in memory 113. Subroutine 450a includes instructions for the simultaneous activation of all active auditory, visual, and/or tactile stimulus sources. Optionally, the activation of all sources may include the activation of tactile stimulation to run throughout all subsequent auditory and/or visual stimulation. Another exemplary subroutine 450b may include instructions for alternating the left auditory, visual, and/or tactile stimulus sources with the right auditory, visual, and/or tactile stimulus sources (i.e., the left stimuli and right stimuli take turns being active.) Another exemplary subroutine 450c may include instructions for alternating the visual sources with the auditory and/or tactile sources (i.e., the visual stimuli and the auditory/tactile stimuli take turns being active.) Another exemplary subroutine 450d may include instructions for alternating the left auditory and/or tactile source and the right visual source with the right auditory and/or tactile source and the left visual source (i.e., opposite auditory/tactile stimuli take turns being active.).

In certain embodiments, one or more of subroutines 450a, 450b, 450c, or 450d, access the analyzed measurements from subroutine 450e and modifies the instructions they provide to the auditory, visual, and/or tactile stimuli depending on real-time or near real-time measurements of the user obtained from sensor assembly 150. Such programming is further described below.

In step 440, programming 450, including by not limited to subroutines 450a, 450b, 450c, and 450d, may each be applied one or more times, individually or in combination with one another. The programming may, in addition, provide sequences of output in subroutines 450a, 450b, 450c, and 450d at different frequencies and/or timings. Thus, for example the subroutines may provide output at specific frequencies that change as the subroutine is repeated. Thus, for example, subroutine 450a may provide auditory output to vibration source 120R or 120L at a frequency of 256 Hz that is turned on and off, that is it is pulsed, at a pulse frequency of 1 Hz for 2 minutes. This square pulse auditory signal thus generates signals at a frequency of 1 Hz in addition to higher harmonics. At a subsequent time, the output at 256 Hz is pulsed at twice the previous pulse frequency for 2 minutes. In this manner, the auditory frequency of 256 Hz may be modulated over a wide range, including frequencies corresponding to brain wave frequencies.

In addition, by alerting the output between left and right channels, the brain may be stimulated in a way that it is forced to communicate between the left and right sides of the brain. This forced communication, for example, can allow PTSD memories to be wired to both sides of the brain, thereby stopping undesirable flashbacks.

In step 440, subroutine 450e receives measurements from sensor assembly 150 and stores analyzed measurements. In one embodiment, sensor assembly 150 provides instantaneous, or nearly instantaneous, measurements from the user. Thus, for example and without limitation, sensor assembly 150 provides a sequence of measurements of beat-to-beat intervals of the heart of the user, that is, the time interval between the last two heart beats, which is also referred to, without libation, as the NN intervals. Controller 130 then computes and stores values of the heart rate variability (HRV), which is a mathematical representation of the physiological phenomenon of variation in the time interval between heartbeats.

In another embodiment, sensor assembly 150 provides accelerometer data, which is stored by controller 130 and used to modify stimuli to the user. The accelerometer provides data on the movement of the user and is used to provide information related to the user's respiration rate and eye movement. The accelerometer is sensitive to movement of the wearer and in certain embodiment provides an indication of eye motion. The accelerometer may be calibrated to determine signals that correspond to REM sleep, which may be stored in memory 133. The accelerometer information may then be used by controller 130 to determine if the user is experiencing REM sleep. When this is found to be the case, controller 130 may reduce the brightness and/or volume of the stimuli at a rate, for example, of 20% every 20 secs, until the light and/or sound are turned off.

In yet another embodiment, sensor assembly 150 includes a thermocouple or other temperature sensor that provides data on the temperature of the user, which is stored by controller 130 and which is used determine a stage of sleep of the user. The thermocouple may be calibrated to determine signals that correspond to REM sleep, which may be stored in memory 133. The temperature measurement may then be used by controller 130 to determine if the user is experiencing REM sleep. When this is found to be the case, controller 130 may reduce the brightness and/or volume of the stimuli at a rate, for example, of 20% every 20 sec, until the light and/or sound are turned off.

In another embodiment, sensor assembly 150 provides EEG data from the user, which is stored by controller 130 and which is used to modify stimuli to the user. The EEG data may be used to determine how relaxed the user is and if there is any hemispheric imbalance. Thus, for example, if the EEG data indicates that one side of the brain is consistently more active than the other side, the stored EEG data can be used to increase stimuli to that other side of the brain.

In one embodiment, a time-domain calculation of NN intervals is used to compute the HRV. Thus, for example, the sequence of NN intervals ("$NN_i$") is accepted from sensor assembly 150 and stored in memory 133. After the accumulation NNi for a period of time, T, the HRV is calculated as approximated by the root mean square of successive differences between adjacent NNs, or RMSSD. Thus, at a time T from the beginning of the accumulation of data, if N consecutive NN intervals are stored in memory 133, the following calculation is performed in processor 134 according to a program stored in the memory:

$$RMSSD = \sqrt{\frac{1}{N-1}\left(\sum_{i=1}^{N-1}(NN_{i+1} - NN_i)^2\right)}$$

The initial value of RMSSD (that is, $RMSSD_0$) is stored in memory 133 as a baseline. Thereafter, at the end of each period T, the calculation of RMSSD is repeated covering that time period. As a result, a sequence of $RMSSD_j$ values are computed. Next the difference between the current RMSSD value and the baseline $RMSSD_0$ is computed as $\Delta RMSSDj = RMSSD_j - RMSSD_0$. $\Delta RMSSD$ is a measure of the change between the current HRV and the baseline, initial HRV.

In general, it is realized by those skilled in the art, that an increased in HRV is associated with a relaxed state, or a sleep state, and that a decrease in HRV is associated with a less relaxed, or stressed, state. For uses of therapeutic system 100 intended to calm a person or to induce sleep, a positive $\Delta RMSSD$ indicates that the person is becoming relaxed and that the system is working as intended. A negative $\Delta RMSSD$ indicates that the person is not becoming more relaxed. In one embodiment, an indication that the person is relaxed ($\Delta RMSSD > 0$) is used to modify the treatment by reducing the treatment time and/or intensity of the stimuli, and an indication that the person is less relaxed ($\Delta RMSSD < 0$) is used to modify the treatment to increase the treatment time and/or the intensity of the stimuli.

Thus, for example an without limitation, if $-10\% < \Delta RMSSD < +10\%$, no change is made to the stimuli, if $\Delta RMSSD > +10\%$, then the treatment time and/or stimuli is decreased (for example by decreasing the time and/or intensity of stimuli by 10%), and if $\Delta RMSSD < -10\%$, then the treatment time and/or stimuli is increased (for example by increasing the time and/or intensity of stimuli by 10%).

The calculations described above are provided by way of explanation, and are not meant to limit the scope of the calculations or how the operation of therapeutic system 100 is or is not modified using HRV measurements.

Although the above steps show method 400 of treating a patient in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the treatment.

One or more of the steps of the method 400 may be performed with the circuitry as described herein, for example, circuitry of the controller 130 or the external control unit 130a such as one or more of a processor or logic circuitry such as a central processing unit (CPU) or a programmable array logic for field programmable gate array. The circuitry may be programmed to provide one or more of the steps of the method 400, and the program may comprise program instructions stored on a computer readable memory or programmed steps of the logic circuitry such as the programmable array logic or the field programmable gate array, for example.

EXAMPLE 1

The following describes an example of a stimulation pattern that has been found by empirical studies to be effective for inducing sleep, including napping, increasing neuroplasticity, treating brain injuries from strokes, TBI, or mTBI, improving balance, including improving fine motor control and reaction times, and treating PTSD, to name a few indications.

Light and auditory stimulus at a first frequency may be provided for a first time segment, then at a second lower frequency for a second time segment, and then at a third lower frequency for a third time segment. Each time segment may include one or more sub-segments of light and auditory stimulus, each sub-segment comprising one of the subroutines described above, for example. The light and auditory stimulus may end after a pre-determined time period, such as 20 minutes. The light and auditory stimulus may be ramped back up (i.e., starting from the third frequency, then transitioning to the second frequency, and finally transitioning to the third frequency), such as to wake the user. Alternatively or in combination, the light and auditory stimulus may be maintained at the second frequency such as to maintain a sleep state of the user. As described above, tactile stimulus may be provided concurrently with the auditory stimulus. The light may be provided at a wavelength of 580 nm and the auditory having a frequency of 256 Hz may be provided, or any of a number of auditory frequencies or combinations thereof that the subject can select as they wish.

Table 1 below describes an exemplary treatment regimen for this example. The stimulation provided in Table 1 first cycles through a block of four Segment A outputs, then cycles through a block of four Segment B outputs, then cycles through seven blocks of four Segment C outputs, and lastly repeats the block of four Segment A outputs. For Segment A outputs (A1, A2, A3, and A4), the auditory and light outputs cycle 115 or 116 times between being on for 0.1277 seconds and then being off for 0.1277 seconds (that is, at a pulse frequency of 3.9 Hz), followed by no output for 0.5 seconds. For Segment B outputs (B1, B2, B3 and B4), the auditory and light outputs cycle 44 or 45 times between being on for 0.3333 seconds and then being off for 0.3333 seconds (that is, at a pulse frequency of 1.5 Hz) followed by no output for 0.5 seconds. For Segment C outputs (C1, C2, C3 and C4), the auditory and light outputs cycle 14 or 15 times between being on for 1 second and then being off for 1 second (that is, a pulse frequency of 0.5 Hz), followed by no output for 1 second. Segments A1, B1, and C1 pulse the right and left sides of both the light and auditory together, with all outputs are synchronized to be on or off at the same time, as provided by subroutine 450a. Segments A2, B2, and C2 synchronize the left side light and auditory output, and the right side light and auditory output to be opposite to one another, as provided by subroutine 450b. Segments A3, B3, and C3 synchronize both lights together to be opposite to both auditory outputs, as provided by subroutine 450c. Segments A4, B4, and C4 synchronize the right auditory and light to be opposite to the left auditory and light outputs, as provided by subroutine 450d.

In one embodiment, subroutine 450e uses heart rate data to modify the treatment shown in Table 1 as follows. Table 1 lists a temporal sequence of stimuli. During the execution of each segment, if the current value of $\Delta RMSSD$ falls within $-10\% < \Delta RMSSD < +10\%$, then the segment is followed as listed in Table 1. If during each segment the current value of $\Delta RMSSD$ is greater than $+10\%$, then the treatment time and/or stimuli is decreased. This may be accomplished, for example and without limitation, by decreasing the length of time of the current segment by 10%, and/or by decreasing the amplitude of the stimuli (that is, the intensity of stimuli provided to the user) by 10%. If during each segment the current value of $\Delta RMSSD$ is less than $-10\%$, then the treatment time and/or stimuli is increased. This may be accomplished, for example and without limitation, by increasing the length of time of the current segment by 10%, and/or by increasing the amplitude of the stimuli (that is, the intensity of stimuli provided to the user) by 10%.

In another embodiment, sensor assembly 150 provides accelerometer data, which is stored by controller 130 and used to modify stimuli to the user by aiding in the detection of REM sleep where HRV data alone might be insufficient to determine the relaxation state of the users. In yet another embodiment, sensor assembly 150 provides data on the temperature of the user, which is stored by controller 130 and which is used to modify stimuli to the user. The temperature data is used to refine the sleep staging and modifying the stimuli accordingly. Thus, for example, a lower temperature indicates deeper sleep level, and the stimuli is modified to reduce the intensity of the light and audio. Further, sub-patterns having the greatest relaxation effects are prioritized, and may, for example, reduce the light and/or sound intensity 10%, finish the sub-pattern, and continue to repeat the sub-pattern until the HRV level indicates that the person is asleep.

In another embodiment, sensor assembly 150 provides EEG data from the user, which is stored by controller 130 and which is used to modify stimuli to the user. The EEG data may be used to determine how relaxed the user is and if there is any hemispheric imbalance. Thus, for example, if the EEG data indicates that the right side of the brain is consistently more active than the stored EEG data can be used to increase stimuli to the opposite side of the brain. This measuring of hemispheric imbalance can also be used as a measure of recovery from concussion, TBI and mTBI. And as a proxy for likely improvements in balance, fine motor skills and reaction speeds, all of which are hampered by hemispheric imbalance.

TABLE 1

|  | Auditory Left | Auditory Right | Light Left | Light Right |
|---|---|---|---|---|
| Segments A1-A4 for 120 s | | | | |
| Segment A1 (Light and Auditory both sides pulse together) Repeat 116 times, followed by 0.5 sec gap | On 0.1277 s Off 0.1277 s | On 0.1277 s Off 0.1277 s | On 0.1277 s Off 0.1277 s | On 0.1277 s Off 0.1277 s |
| Segment A2 (light and auditory on left side, alternating light and auditory on Right). Repeat 116 times, followed by 0.5 sec gap | On 0.1277 s Off 0.1277 s | Off 0.1277 s On 0.1277 s | On 0.1277 s Off 0.1277 s | Off 0.1277 s On 0.1277 s |
| Segment A3 (both lights together, alternating with both auditory signals together) Repeat 115 times, followed by 0.5 sec gap | On 0.1277 s Off 0.1277 s | On 0.1277 s Off 0.1277 s | Off 0.1277 s On 0.1277 s | Off 0.1277 s On 0.1277 s |
| Segment A4 (auditory left and light right together, alternating auditory right and light left together) Repeat 115 times, followed by 0.5 sec gap | On 0.1277 s Off 0.1277 s | Off 0.1277 s On 0.1277 s | Off 0.1277 s On 0.1277 s | On 0.1277 s Off 0.1277 s |
| Segments B1-B4 for 120 s | | | | |
| Segment B1 (Light and Auditory both sides pulse together) Repeat 45 times, followed by 0.5 sec gap | On 0.3333 s Off 0.3333 s | On 0.3333 s Off 0.3333 s | On 0.3333 s Off 0.3333 s | On 0.3333 s Off 0.3333 s |
| Segment B2 (light and auditory on left side, alternating light and auditory on Right) Repeat 44 times, followed by 0.5 sec gap | On 0.3333 s Off 0.3333 s | Off 0.3333 s On 0.3333 s | On 0.3333 s Off 0.3333 s | Off 0.3333 s On 0.3333 s |
| Segment B3 (both lights together, alternating with both auditory signals together) Repeat 44 times, followed by 0.5 sec gap | On 0.3333 s Off 0.3333 s | On 0.3333 s Off 0.3333 s | Off 0.3333 s On 0.3333 s | Off 0.3333 s On 0.3333 s |
| Segment B4 (auditory left and light right together, alternating auditory right and light left together) Repeat 44 times, followed by 0.5 sec gap Repeat the following Segments C1-C4 7 times for a total of 14 minutes | On 0.3333 s Off 0.3333 s | Off 0.3333 s On 0.3333 s | Off 0.3333 s On 0.3333 s | On 0.3333 s Off 0.3333 s |
| Segment C1 (Light and Auditory both sides pulse together) Repeat 15 times, followed by 1 sec gap | On 1 sec Off 1 sec | On 1 sec Off 1 sec | On 1 sec Off 1 sec | On 1 sec Off 1 sec |

TABLE 1-continued

| | Auditory Left | Auditory Right | Light Left | Light Right |
|---|---|---|---|---|
| Segment C2 (light and auditory on left side, alternating light and auditory on Right) Repeat 15 times, followed by 1 sec gap | On 1 sec Off 1 sec | Off 1 sec On 1 sec | On 1 sec Off 1 sec | Off 1 sec On 1 sec |
| Segment C3 (both lights together, alternating with both auditory signals together) Repeat 14 times, followed by 1 sec gap | On 1 sec Off 1 sec | On 1 sec Off 1 sec | Off 1 sec On 1 sec | Off 1 sec On 1 sec |
| Segment C4 (auditory left and light right together, alternating auditory right and light left together) Repeat 14 times, followed by 1 sec gap Segments A1-A4 for 120 s | On 1 sec Off 1 sec Off 1 sec | Off 1 sec On 1 sec On 1 sec | Off 1 sec On 1 sec On 1 sec | On 1 sec Off 1 sec Off 1 sec |
| Segment A1 (Light and Auditory both sides pulse together) Repeat 116 times, followed by 0.5 sec gap | On 0.1277 Off 0.1277 | On 0.1277 Off 0.1277 | On 0.1277 Off 0.1277 | On 0.1277 Off 0.1277 |
| Segment A2 (light and auditory on left side, alternating light and auditory on Right) Repeat 116 times, followed by 0.5 sec gap | On 0.1277 Off 0.1277 | Off 0.1277 On 0.1277 | On 0.1277 Off 0.1277 | Off 0.1277 On 0.1277 |
| Segment A3 (both lights together, alternating with both auditory signals together) Repeat 115 times, followed by 0.5 sec gap | On 0.1277 Off 0.1277 | On 0.1277 Off 0.1277 | Off 0.1277 On 0.1277 | Off 0.1277 On 0.1277 |
| Segment A4 (auditory left and light right together, alternating auditory right and light left together) Repeat 115 times, followed by 0.5 sec gap | On 0.1277 Off 0.1277 | Off 0.1277 On 0.1277 | Off 0.1277 On 0.1277 | On 0.1277 Off 0.1277 |

EXAMPLE 2

The following describes an example of a stimulation pattern that has been found by empirical studies to be effective for inducing sleep. The stimulation pattern of Example 2 includes the part of the treatment regimen shown in Table 1. Specifically, the stimulation first cycles through a block of four Segment A outputs, then cycles through a block of four Segment B outputs, and then cycles through seven blocks of four Segment C outputs. The repetition of the last block of four Segment A outputs is not provided in Example 2.

The modification of the segments using subroutine 450e is the same as in Example 1.

EXAMPLE 3

The following described example of a stimulation pattern that has been found by empirical studies to be effective for increasing alpha wave brain activity, inducing neuroplasticity, treating stroke or other brain injuries such as TBI, mTBI, including improving balance, improving fine motor control and reaction times, and treating PTSD, to name a few indications.

HRV is used in the case of TBI and mTBI and PTSD as well—typically a relaxation effect is measured after the device has induced neuroplasticity—the stimulus is maintained at a standard level until that relaxation effect is measured, and then the device shifts towards a sleep modality to help improvements in balance that have occurred.

In this example, the four subroutines described above and herein are applied and repeated for multiple time segments, each at a predetermined stimulation (repetition) frequency. The four subroutines may be repeated, such as with each segment of the four subroutines lasting 120 seconds, for example. As described above, tactile stimulus may be provided concurrently with the auditory stimulus. The light may be provided at a wavelength of 580 nm and the auditory having a frequency of 432 Hz may be provided.

Table 2 below describes an exemplary treatment regimen for this example. The stimulation provided in Table 2 cycles through a block of four Segment A outputs 10 times. For Segment A1, A2, A3, and A4, the auditory and light outputs cycle 115 or 116 times between being on for 0.1277 seconds and then being off for 0.1277 seconds, followed by no output for 0.5 seconds. Segments A1 pulses the right and left sides of both the light and auditory together, with all outputs are synchronized to be on or off at the same time, as provided by subroutine 450a. Segment A2 synchronizes the left side light and auditory output, and the right side light and auditory output to be opposite to one another, as provided by subroutine 450b. Segment A3 synchronizes both lights together to be opposite to both auditory outputs, as provided by subroutine 450c. Segment A4 synchronizes the right auditory and light to be opposite to the left auditory and light outputs, as provided by subroutine 450d.

TABLE 2

| Repeat the following Segments A1-A4 10 times for a total time of 20 minutes | Auditory Left | Auditory Right | Light Left | Light Right |
|---|---|---|---|---|
| Segment A1 (Light and Auditory both sides pulse together) Repeat 116 times, followed by 0.5 sec gap | On 0.1277 s Off 0.1277 s | On 0.1277 s Off 0.1277 s | On 0.1277 s Off 0.1277 s | On 0.1277 s Off 0.1277 s |
| Segment A2 (light and auditory on left side, alternating light and auditory on Right) Repeat 116 times, followed by 0.5 sec gap | On 0.1277 s Off 0.1277 s | Off 0.1277 s On 0.1277 s | On 0.1277 s Off 0.1277 s | Off 0.1277 s On 0.1277 s |
| Segment A3 (both lights together, alternating with both auditory signals together) Repeat 115 times, followed by 0.5 sec gap | On 0.1277 s Off 0.1277 s | On 0.1277 s Off 0.1277 s | Off 0.1277 s On 0.1277 s | Off 0.1277 s On 0.1277 s |
| Segment A4 (auditory left and light right together, alternating auditory right and light left together) Repeat 115 times, followed by 0.5 sec gap | On 0.1277 s Off 0.1277 s | Off 0.1277 s On 0.1277 s | Off 0.1277 s On 0.1277 s | On 0.1277 s Off 0.1277 s |

EXAMPLE 4

The following described yet another example of a stimulation pattern that has been found by empirical studies to be effective for increasing energy levels in the subject. Light and auditory stimulus at a first frequency may be provided for a first time segment, then at a second higher frequency for a second time segment, then back at the first frequency for a subsequent time segment, and so forth. Each time segment may include one or more sub-segments of light and auditory stimulus, each sub-segment comprising one of the subroutines described above, for example. The light and auditory stimulus may end after a pre-determined time period, such as 20 minutes. As described above, tactile stimulus may be provided concurrently with the auditory stimulus. The light may be provided at a wavelength of 580 nm and the auditory having a frequency of 432 Hz may be provided.

HRV is used to determine the effectiveness of the stimulation—when HRV drops, it indicates an arousal effect, and in the exact reversal of sleep induction, in this mode, where arousal effect is noted in some sub-routines more than others, then these sub-routines are prioritized. When it is desired to wake up the user, the time of a sub-segment for increasing arousal may be increased.

Table 3 below describes an exemplary treatment regimen for this example. The stimulation provided in Table 3 cycles ten times first through a block of four Segment A outputs, then through a block of four Segment D outputs. For Segment A outputs (A1, A2, A3, and A4), the auditory and light outputs cycle 115 or 116 times between being on for 0.1277 seconds and then being off for 0.1277 seconds, followed by no output for 0.5 seconds. For Segment D outputs (D1, D2, D3 and D4), the auditory and light outputs cycle 44 or 45 times between being on for 0.0667 seconds and then being off for 0.0667 seconds, followed by no output for 0.5 seconds. Segments A1 and D1 pulse the right and left sides of both the light and auditory together, with all outputs are synchronized to be on or off at the same time, as provided by subroutine 450a. Segments A2 and D2 synchronize the left side light and auditory output, and the right side light and auditory output to be opposite to one another, as provided by subroutine 450b. Segments A3 and D3 synchronize both lights together to be opposite to both auditory outputs, as provided by subroutine 450c. Segments A4 and D4 synchronize the right auditory and light to be opposite to the left auditory and light outputs, as provided by subroutine 450d.

TABLE 3

| Repeat 10 times: Segments A1-A4 followed by Segments D1-D4, for a total time of 20 minutes | Auditory Left | Auditory Right | Light Left | Light Right |
|---|---|---|---|---|
| Segment A1 (Light and Auditory both sides pulse together) Repeat 116 times, followed by 0.5 sec gap | On 0.1277 s Off 0.1277 s | On 0.1277 s Off 0.1277 s | On 0.1277 s Off 0.1277 s | On 0.1277 s Off 0.1277 s |
| Segment A2 (light and auditory on left side, alternating light and auditory on Right) Repeat 116 times, followed by 0.5 sec gap | On 0.1277 s Off 0.1277 s | Off 0.1277 s On 0.1277 s | On 0.1277 s Off 0.1277 s | Off 0.1277 s On 0.1277 s |

TABLE 3-continued

| Repeat 10 times: Segments A1-A4 followed by Segments D1-D4, for a total time of 20 minutes | Auditory Left | Auditory Right | Light Left | Light Right |
|---|---|---|---|---|
| Segment A3 (both lights together, alternating with both auditory signals together) Repeat 115 times, followed by 0.5 sec gap | On 0.1277 s Off 0.1277 s | On 0.1277 s Off 0.1277 s | Off 0.1277 s On 0.1277 s | Off 0.1277 s On 0.1277 s |
| Segment A4 (auditory left and light right together, alternating auditory right and light left together) Repeat 115 times, followed by 0.5 sec gap | On 0.1277 s Off 0.1277 s | Off 0.1277 s On 0.1277 s | Off 0.1277 s On 0.1277 s | On 0.1277 s Off 0.1277 s |
| Segment D1 (Light and Auditory both sides pulse together) Repeat 221 times, followed by 0.5 sec gap | On 0.0667 s Off 0.0667 s | On 0.0667 s Off 0.0667 s | On 0.0667 s Off 0.0667 s | On 0.0667 s Off 0.0667 s |
| Segment D2 (light and auditory on left side, alternating light and auditory on Right) Repeat 221 times, followed by 0.5 sec gap | On 0.0667 s Off 0.0667 s | Off 0.0667 s On 0.0667 s | On 0.0667 s Off 0.0667 s | Off 0.0667 s On 0.0667 s |
| Segment D3 (both lights together, alternating with both auditory signals together) Repeat 221 times, followed by 0.5 sec gap | On 0.0667 s Off 0.0667 s | On 0.0667 s Off 0.0667 s | Off 0.0667 s On 0.0667 s | Off 0.0667 s On 0.0667 s |
| Segment D4 (auditory left and light right together, alternating auditory right and light left together) Repeat 221 times, followed by 0.5 sec gap | On 0.0667 s Off 0.0667 s | Off 0.0667 s On 0.0667 s | Off 0.0667 s On 0.0667 s | On 0.0667 s Off 0.0667 s |

EXAMPLE 5

The following Table 4 lists experimental results for the use of the inventive methods. The table lists what was being tested or treated, details of the conditions, the number of subjects, and the results of the tests. In each case, the stimulation in Example 1 for treating non-sleep related problems and for inducing a short sleep, and the stimulation in Example 2 was used for all other treatments.

This is modified by changing brightness and volume, but also selected which of the four subsections, is working to produce the most stable rMSSD. And will adjust accordingly Several of the treatments provided improvements in physical and/or mental performance, such as improving fine motor control and reaction times. This may be due to the device providing improved neuroplasticity in the days after treatment. Other treatments provided improvements in performing tasks and recovery from brain injury, such as injuries resulting from oxygen deprivation (strokes) and for those suffering from traumatic brain injury (TBI) or mild traumatic brain injury, and my provide improving balance, improving fine motor control. Other treatments provided relief to sufferers of PTSD by reducing the subject's response to triggering stimuli.

TABLE 4

| Treatment For | Details | No. of subjects | Results |
|---|---|---|---|
| Pain Management | Reduction of chronic nerve damage pain and improvement of sleep on self. Use of device for 3 months with 20 min/day of use of device | 1 | Eliminated chronic nerve damage pain for the time the device was used. |
| PTSD | Treating PTSD. Device use time of 5 hours. | 3 | Reduced flashbacks, nightmares and hypervigilance in all 3 subjects |
| Performance Enhancement | Marksmanship (rifles and pistols), endurance and speed driving (advanced surveillance, coordination and evasion). 6 hours training each subject. | 20 | Significant improvements in marksmanship in all participants and ease of concentration during speed driving, faster times on endurance trials for 19/20 subjects |
| Performance Enhancement | Fine motor skills on bomb disposal personnel 3 hours training with device | 3 | Improved performance of fine motor skills on bomb disposal VR simulation for all subjects |

TABLE 4-continued

| Treatment For | Details | No. of subjects | Results |
|---|---|---|---|
| Performance Enhancement | Fine motor skills of surgeons-3 hours training each | 3 | Improved performance of fine motor skills on surgical procedures VR simulation for all subjects. |
| Performance Enhancement | Pistol use and marksmanship. 3 hours training | 2 | 10% and 30% respectively increased speed in stripping and reassembling weapons. (average each of 5 tests, pre and post training) 6% average improvement in marksmanship scores - highly significant for such level of skill for all subjects |
| Performance Enhancement and PTSD | Performance by anti-terror and anti-drug squads of an elite firearms unit of a police force. 3 hours training each. | 5 | 10% average improvement in scores. Total absence of any PTSD |
| Performance Enhancement | Marksmanship. 2 hours training | 1 | average grouping shrunk from 5 inches to 1 inch at 200 yds. |
| Brain State | Increasing alpha activity. 4 hours total training time per subject. Group 1 L&S stimulation and biofeedback. Group 2 - just L&S stimulation Group 3 just biofeedback, Group 4 control. Double blinded - those administering had no idea of what was predicted to happen | 20 | Results as predicted. Group 1 greatest change, followed by group 2, Group 3 least change of active groups. Group 4 no change. |
| Performance Enhancement | Marksmanship. | 3 + 15 | Significant improvement for all subjects. |
| Mental Performance Enhancement | Attention, learning and resistance to interrogation - 4 hours each person. Conduct after Capture course. | 3 | positive reports from all subjects |
| Performance Enhancement | Motion sickness for fixed wing aircraft pilots who have developed problems. 4 hours training per subject | 4 | Dramatic improvements in half of subjects. Small improvements in remaining half of subjects |
| PTSD | PTSD symptoms - test to remove neurological symptoms of flashbacks, nightmares and cold sweats | 33 | Successful in 31/33 subjects |
| Performance Enhancement | Driver performance using VR simulators for reaction speeds and performance under stress | 2 | Immediate increase in reaction speeds and improved performance for all subjects |
| Performance Enhancement | Professional soccer player performance. Trained for 4 hours. Battery of 21 tests | 1 | 5-25% increase in speeds to complete tests |
| Inducing Sleep | Sleep patterning and circadian rhythm adjustment for crews setting endurance records. members each year. Also used for improving safety drills when parachuting | 6 | All subjects fell asleep using the device during training, including one subject that was ill with a virus and couldn't otherwise sleep. |
| Performance Enhancement | Race car driver performance. Ten days of training for 30 minutes per day. | 1 | Subject won his first Grand Prix of the season. |
| Performance Enhancement | Soccer player kicking performance. 5 days of 1 hour each day | 1 | Subject went from 5th ranked to highest ranked |
| Stroke Recovery | Use on 6 year post stroke subjects. four hours training. | 10 | Observable balance improvement in 7/10 subjects. 3 subjects had had dramatic improvements in their sleep. |
| Epilepsy Seizure Reduction | Effect on seizures of photosensitive epileptics. 4 hours training | 3 | One subject was found to not be epileptic. The other two subjects had a reduction in both severity and frequency of seizures, for at least a period of at least one month. |
| Concussion Recovery | Effect on concussions | 18 | All subjects appeared to have recovery happen at very fast speed. |
| Performance Enhancement | Effect on musical ability of a jazz musician. | 1 | Greatly improved performance speed |
| PTSD | PTSD. Treatment protocol lasting 3 sessions of 2 hours each | 22 | 19 individuals saw a cessation of major symptoms - flashbacks, nightmares, cold sweats and hypervigilance. the remaining 3 appeared to be calmer after treatment, but did not stop the major neurological symptoms |
| Sleep | Insomnia | 1 | Goes to sleep 4 times in 45 mins |
| Pain Management | Chronic Regional Pain Syndrome | 1 | Subject had constant pain on touching arms with no relief in 3 years Subject |

TABLE 4-continued

| Treatment For | Details | No. of subjects | Results |
|---|---|---|---|
| | | | saw immediate pain relief on first use of the device. Continued use over the following weeks results in periods of time without pain grow up to four hours following each use. Averaging at two hours. |
| Pain Management and Sleep | Chronic pain | 1 | After six months of use, the subject continues getting 30% more sleep, and a significant reduction in pain. Device continues to be used 3-4 times a week for 20 min. |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby. The invention includes all of the different combinations embodied herein.

It is to be understood that the invention includes all of the different combinations embodied herein. Throughout this specification, the term "comprising" shall be synonymous with "including," "containing," or "characterized by," is inclusive or open-ended and does not exclude additional, unrecited elements or method steps. "Comprising" is a term of art which means that the named elements are essential, but other elements may be added and still form a construct within the scope of the statement. "Comprising" leaves open for the inclusion of unspecified ingredients even in major amounts.

What is claimed is:

1. A method of providing stimulation to a user for a treatment time, the method comprising:
   providing a headset to be worn by the user, where the headset includes four stimuli sources including a left light source activated to provide visual stimuli to a left eye of the user, a right light source activated to provide visual stimuli to a right eye of the user, a left vibration source activated to provide auditory stimuli to the left side of a head of the user, and a right vibration source activated to provide auditory stimuli to the right side of the head;
   obtaining a measurement of the user using at least one sensor;
   determining a state of the user from the obtained measurement;
   activating each of said stimuli sources between a high stimuli and a low stimuli at a stimulation frequency for a period of time, where at least part of said activating includes activating at least two of said four stimuli sources out of phase with the activating of at least two other of the four stimuli sources; and
   modifying said activating according to said determined state of the user;
   where said activating includes alternating between
      synchronously activating said four stimuli sources for a period of time,
      synchronously activating said left light source and said left vibration source out of phase with said right light source and said right vibration source for a period of time,
      synchronously activating said left light source and said right light source out of phase with said left vibration source and said right vibration source for a period of time, and
      synchronously activating said left light source and said right vibration source out of phase with said left vibration source and said right light source for a period of time.

2. The method of claim 1, where modifying includes modifying said stimulation frequency of said four stimuli sources.

3. The method of claim 1, where modifying includes modifying a temporal length of said activating of said four stimuli sources.

4. The method of claim 1, where modifying includes modifying a high stimuli level of at least one stimuli source of said four stimuli sources.

5. The method of claim 1, where said at least one sensor includes at least one heart rate sensor, at least one heart rate variability (HRV) sensor, at least one temperature sensor, at least one motion sensor, at least one galvanic skin response sensor, at least one accelerometer, at least one EEG sensor, or at least one EMG sensor.

6. The method of claim 5, where said determined state of the user is a state of sleep or a level of relaxation or arousal or a change in the level of relaxation or arousal.

7. The method of claim 6, where said modifying includes modifying a high stimuli level of said left vibration source and said right vibration source.

8. The method of claim 6, and where said modifying includes modifying a high stimuli level of said left light source and said right light source.

9. The method of claim 6, where said modifying said activating according to said determined state of the user includes modifying a temporal length of said activating of said four stimuli sources.

10. The method of claim 6, where said activating includes activating each of said stimuli sources at a first stimulation frequency for a first period of time and activating each of said stimuli sources at a second stimulation frequency for a second period of time;
    where said first stimulation frequency is in a first frequency range of 1.0 and 3.0 Hz, 3.0 to 7.0 Hz, 7.0 to 12 Hz, 12 to 38 Hz or 38 to 42 Hz;

where said second stimulation frequency is in a second frequency range of 1.0 and 3.0 Hz, 3.0 to 7.0 Hz, 7.0 to 12 Hz, 12 to 38 Hz or 38 to 42 Hz; and where said first stimulation frequency is in a different frequency range than said second stimulation frequency range.

11. The method of claim 6, where said determined state of the user is a state of sleep determined to be REM sleep, where said modifying said activating according to said determined state of the user includes reducing a high stimuli level of at least one of said four stimuli sources.

12. The method of claim 11, where said at least one sensor includes two or more sensors, the two or more sensors including:

a first sensor including one of the at least one HRV sensor or one of the at least one heart rate sensor; and a second sensor including one of the at least one temperature sensor, one of the at least one EMG sensor, one of the at least one EEG sensor, or one of the at least one accelerometer.

13. The method of claim 11, where said modifying said activating according to said determined state of the user includes reducing a stimuli level of each of the four stimuli sources until the stimuli sources are turned off.

14. The method of claim 13, where said modifying said activating according to said determined state of the user includes reducing the stimuli level of each of the four stimuli sources by approximately 20% approximately every 20 seconds.

15. The method of claim 6, where said at least one sensor includes the at least one heart rate sensor or the at least one heart rate variability (HRV) sensor, where said determined state of the user is a state of relaxation or a sleep state, where the state of relaxation or the sleep state is indicated by the HRV as determined based on information from the at least one heart rate sensor or the at least one HRV sensor.

16. The method of claim 15, where said determined state of the user is the state of relaxation or the sleep state indicated by an increase in HRV, and where said modifying said activating according to said determined state of the user includes reducing a stimuli level of each of four stimuli sources until the stimuli sources are turned off and/or shortening the treatment time.

17. The method of claim 15, where said determined state of the user is a less relaxed state or a less stressed state indicated by a decrease in HRV, and where said modifying said activating according to said determined state of the user includes increasing a stimuli level of each of the four stimuli sources and/or increasing the treatment time.

18. The method of claim 5, where said determined state of the user is a hemispheric imbalance of brainwaves, where said at least one sensor includes the at least one EEG sensor, where said state is the hemispheric imbalance of brainwaves includes a more active hemisphere of a brain, and where said modifying said activating according to said determined state of the user includes increasing the high stimuli level stimuli sources to a less active hemisphere of the brain.

19. A device to provide stimulation to a user for a treatment time, the device comprising:

a headset to be worn by the user, where the headset includes four stimuli sources including a left light source activated to provide visual stimuli to a left eye of the user, a right light source activated to provide visual stimuli to a right eye of the user, a left vibration source activated to provide auditory stimuli to the left side of a head of the user, and a right vibration source activated to provide auditory stimuli to the right side of the head;

at least one sensor to obtain a measurement of the user; and a processor programmed to
receive said measurement;
determine a state of the user from the measurement;
activate each of said stimuli sources between a high stimuli and a low stimuli at a stimulation frequency for a period of time, where at least part of said activating includes activating at least two of said four stimuli sources out of phase with the activating of at least two other of the four stimuli sources, and
modify the activation of each of said stimuli sources according to said state of the user;

where said processor is programmed to alternate between
synchronously activating said four stimuli sources for a period of time,
synchronously activating said left light source and said left vibration source out of phase with said right light source and said right vibration source for a period of time,
synchronously activating said left light source and said right light source out of phase with said left vibration source and said right vibration source for a period of time, and
synchronously activating said left light source and said right vibration source out of phase with said left vibration source and said right light source for a period of time.

20. The device of claim 19, where said at least one sensor includes one or more of a heart rate sensor, a heart rate variability (HRV) sensor, a temperature sensor, a motion sensor, a galvanic skin response sensor, an accelerometer, an EEG sensor, or an EMG sensor.

21. The device of claim 19, where the state of the user is a state of sleep or a level of relaxation or arousal or a change in the level of relaxation or arousal determined from a temperature sensor, a heart rate or a HRV sensor.

22. The device of claim 19, where said processor is programmed to modify the activation of each of said stimuli sources according to said state of the user includes one or more of changing a high stimuli level of at least one of said four stimuli sources, the stimulation frequency, or the treatment time.

23. The device of claim 19, where the state of the user is a state of hemispheric imbalance of brainwaves, where said at least one sensor includes at least one EEG sensor, where the processor is programmed to increase the high stimuli level stimuli sources to a less active hemisphere of a brain.

* * * * *